(12) United States Patent
Santra et al.

(10) Patent No.: US 10,576,328 B2
(45) Date of Patent: Mar. 3, 2020

(54) SYSTEM AND METHOD FOR CONTACTLESS SENSING ON A TREADMILL

(71) Applicant: Infineon Technologies AG, Neubiberg (DE)

(72) Inventors: Avik Santra, Munich (DE); Ashutosh Baheti, Munich (DE); Jagjit Singh Bal, Fremont, CA (US); Saverio Trotta, Munich (DE)

(73) Assignee: Infineon Technologies AG, Neubiberg (DE)

( * ) Notice: Subject to any disclaimer, the term of this patent is extended or adjusted under 35 U.S.C. 154(b) by 139 days.

(21) Appl. No.: 15/890,155

(22) Filed: Feb. 6, 2018

(65) Prior Publication Data

US 2019/0240535 A1    Aug. 8, 2019

(51) Int. Cl.
    *A63B 24/00*       (2006.01)
    *G01C 22/00*      (2006.01)
                (Continued)

(52) U.S. Cl.
    CPC ............ *A63B 24/0062* (2013.01); *A61B 5/05* (2013.01); *A61B 5/486* (2013.01); *A61B 5/4866* (2013.01); *A61B 5/742* (2013.01); *A61B 5/746* (2013.01); *A61B 5/7475* (2013.01); *A63B 22/025* (2015.10); *G01C 22/00* (2013.01);
                (Continued)

(58) Field of Classification Search
    CPC ............ A63B 22/02–0292; A63B 4/00; A63B 4/0062; A63B 4/0087; A63B 2024/0093; G01S 13/06; G01S 13/42; G01S 13/56; G01S 13/87; G01S 7/352; G01C 22/00;
                (Continued)

(56) References Cited

U.S. PATENT DOCUMENTS

| 4,241,347 A | 12/1980 | Albanese et al. |
| 6,147,572 A | 11/2000 | Kaminski et al. |

(Continued)

FOREIGN PATENT DOCUMENTS

| CN | 1463161 A | 12/2003 |
| CN | 1716695 A | 1/2006 |

(Continued)

OTHER PUBLICATIONS

"BT24MTR11 Using BGT24MTR11 in Low Power Applications 24 GHz Rader," Application Note AN341, Revision: Rev 1.0, Infineon Technologies AG, Munich, Germany, Dec. 2, 2013, 25 pages.

(Continued)

*Primary Examiner* — Jennifer Robertson
(74) *Attorney, Agent, or Firm* — Slater Matsil, LLP

(57) ABSTRACT

A treadmill includes a belt, a display, a first sensor having first transmission circuitry for transmitting a first radar beam over the belt and first reception circuitry for detecting a first reflected signal that is a reflection of the first radar beam from a user on the belt, a processor connected to the first sensor, the belt and the display, and a non-transitory computer-readable storage medium storing a program to be executed by the processor. The program includes instructions for determining, according to the first reflected signal, first data associated with a vital sign of the user and displaying, according to the first data, the vital sign on the display.

20 Claims, 16 Drawing Sheets

(51) Int. Cl.

| | | |
|---|---|---|
| *G01S 7/35* | (2006.01) | |
| *G01S 13/06* | (2006.01) | |
| *A61B 5/05* | (2006.01) | |
| *A61B 5/00* | (2006.01) | |
| *A63B 22/02* | (2006.01) | |
| *G01S 13/87* | (2006.01) | |
| *G01S 13/56* | (2006.01) | |
| *G01S 13/42* | (2006.01) | |

(52) U.S. Cl.
CPC .............. *G01S 7/352* (2013.01); *G01S 13/06* (2013.01); *G01S 13/42* (2013.01); *G01S 13/56* (2013.01); *G01S 13/87* (2013.01); *A63B 2024/009* (2013.01); *A63B 2220/89* (2013.01)

(58) Field of Classification Search
CPC ......... A61B 5/05; A61B 5/486; A61B 5/4866; A61B 5/742; A61B 5/7475; A61B 5/746
See application file for complete search history.

(56) References Cited

U.S. PATENT DOCUMENTS

| | | | |
|---|---|---|---|
| 6,414,631 B1 | 7/2002 | Fujimoto | |
| 6,636,174 B2 | 10/2003 | Arikan et al. | |
| 7,048,973 B2 | 5/2006 | Sakamoto et al. | |
| 7,057,564 B2 | 6/2006 | Tsai et al. | |
| 7,171,052 B2 | 1/2007 | Park | |
| 7,317,417 B2 | 1/2008 | Arikan et al. | |
| 7,596,241 B2 | 9/2009 | Rittscher et al. | |
| 7,692,574 B2 | 4/2010 | Nakagawa | |
| 7,873,326 B2 | 1/2011 | Sadr | |
| 7,889,147 B2 | 2/2011 | Tam et al. | |
| 8,228,382 B2 | 7/2012 | Pattikonda | |
| 8,497,805 B2 | 7/2013 | Rofougaran et al. | |
| 8,659,369 B2 | 2/2014 | Rofougaran et al. | |
| 8,731,502 B2 | 5/2014 | Salle et al. | |
| 8,836,596 B2 | 9/2014 | Richards et al. | |
| 8,847,814 B2 | 9/2014 | Himmelstoss et al. | |
| 8,860,532 B2 | 10/2014 | Gong et al. | |
| 8,976,061 B2 | 3/2015 | Chowdhury | |
| 9,172,132 B2 | 10/2015 | Kam et al. | |
| 9,182,476 B2 | 11/2015 | Wintermantel | |
| 9,202,105 B1 | 12/2015 | Wang et al. | |
| 9,413,079 B2 | 8/2016 | Kamgaing et al. | |
| 9,495,600 B2 | 11/2016 | Heu et al. | |
| 9,886,095 B2 | 2/2018 | Pothier | |
| 9,935,065 B1 | 4/2018 | Baheti et al. | |
| 2003/0179127 A1 | 9/2003 | Wienand | |
| 2004/0238857 A1 | 12/2004 | Beroz et al. | |
| 2006/0001572 A1 | 1/2006 | Gaucher et al. | |
| 2006/0049995 A1 | 3/2006 | Imaoka et al. | |
| 2006/0067456 A1 | 3/2006 | Ku et al. | |
| 2007/0210959 A1 | 9/2007 | Herd et al. | |
| 2008/0106460 A1 | 5/2008 | Kurtz et al. | |
| 2008/0238759 A1 | 10/2008 | Carocari et al. | |
| 2008/0291115 A1 | 11/2008 | Doan et al. | |
| 2008/0308917 A1 | 12/2008 | Pressel et al. | |
| 2009/0073026 A1 | 3/2009 | Nakagawa | |
| 2009/0085815 A1 | 4/2009 | Jakab et al. | |
| 2009/0153428 A1 | 6/2009 | Rofougaran et al. | |
| 2009/0315761 A1 | 12/2009 | Walter et al. | |
| 2010/0207805 A1 | 8/2010 | Haworth | |
| 2011/0299433 A1 | 12/2011 | Darabi et al. | |
| 2012/0087230 A1 | 4/2012 | Guo et al. | |
| 2012/0092284 A1 | 4/2012 | Rofougaran et al. | |
| 2012/0116231 A1 | 5/2012 | Liao et al. | |
| 2012/0195161 A1 | 8/2012 | Little et al. | |
| 2012/0206339 A1 | 8/2012 | Dahl | |
| 2012/0245479 A1* | 9/2012 | Ganesh .................. | A61B 5/024 600/508 |
| 2012/0265486 A1 | 10/2012 | Klofer et al. | |
| 2012/0268314 A1 | 10/2012 | Kuwahara et al. | |
| 2012/0280900 A1 | 11/2012 | Wang et al. | |
| 2013/0027240 A1 | 1/2013 | Chowdhury | |
| 2013/0106673 A1 | 5/2013 | McCormack et al. | |
| 2014/0028542 A1 | 1/2014 | Lovitt et al. | |
| 2014/0070994 A1 | 3/2014 | Schmalenberg et al. | |
| 2014/0145883 A1 | 5/2014 | Baks et al. | |
| 2014/0324888 A1 | 10/2014 | Xie et al. | |
| 2015/0181840 A1 | 7/2015 | Tupin, Jr. et al. | |
| 2015/0185316 A1 | 7/2015 | Rao et al. | |
| 2015/0212198 A1 | 7/2015 | Nishio et al. | |
| 2015/0243575 A1 | 8/2015 | Strothmann et al. | |
| 2015/0277569 A1 | 10/2015 | Sprenger et al. | |
| 2015/0325925 A1 | 11/2015 | Kamgaing et al. | |
| 2015/0346820 A1 | 12/2015 | Poupyrev et al. | |
| 2015/0348821 A1 | 12/2015 | Iwanaga et al. | |
| 2015/0364816 A1 | 12/2015 | Murugan et al. | |
| 2016/0018511 A1 | 1/2016 | Nayyar et al. | |
| 2016/0041617 A1 | 2/2016 | Poupyrev | |
| 2016/0041618 A1 | 2/2016 | Poupyrev | |
| 2016/0061942 A1 | 3/2016 | Rao et al. | |
| 2016/0061947 A1 | 3/2016 | Patole et al. | |
| 2016/0098089 A1 | 4/2016 | Poupyrev | |
| 2016/0103213 A1 | 4/2016 | Ikram et al. | |
| 2016/0109566 A1 | 4/2016 | Liu et al. | |
| 2016/0118353 A1 | 4/2016 | Ahrens et al. | |
| 2016/0135655 A1 | 5/2016 | Ahn et al. | |
| 2016/0146931 A1 | 5/2016 | Rao et al. | |
| 2016/0146933 A1 | 5/2016 | Rao et al. | |
| 2016/0178730 A1 | 6/2016 | Trotta et al. | |
| 2016/0187462 A1 | 6/2016 | Altus et al. | |
| 2016/0191232 A1 | 6/2016 | Subburaj et al. | |
| 2016/0223651 A1 | 8/2016 | Kamo et al. | |
| 2016/0240907 A1 | 8/2016 | Haroun | |
| 2016/0249133 A1 | 8/2016 | Sorensen | |
| 2016/0252607 A1 | 9/2016 | Saboo et al. | |
| 2016/0259037 A1 | 9/2016 | Molchanov et al. | |
| 2016/0266233 A1 | 9/2016 | Mansour | |
| 2016/0269815 A1 | 9/2016 | Liao et al. | |
| 2016/0291130 A1 | 10/2016 | Ginsburg et al. | |
| 2016/0299215 A1 | 10/2016 | Dandu et al. | |
| 2016/0306034 A1 | 10/2016 | Trotta et al. | |
| 2016/0320852 A1 | 11/2016 | Poupyrev | |
| 2016/0320853 A1 | 11/2016 | Lien et al. | |
| 2016/0327633 A1 | 11/2016 | Kumar Y.B. et al. | |
| 2016/0334502 A1 | 11/2016 | Ali et al. | |
| 2016/0349845 A1 | 12/2016 | Poupyrev et al. | |
| 2017/0033062 A1 | 2/2017 | Liu et al. | |
| 2017/0045607 A1 | 2/2017 | Bharadwaj et al. | |
| 2017/0052618 A1 | 2/2017 | Lee et al. | |
| 2017/0054449 A1 | 2/2017 | Mani et al. | |
| 2017/0060254 A1 | 3/2017 | Molchanov et al. | |
| 2017/0070952 A1 | 3/2017 | Balakrishnan et al. | |
| 2017/0074974 A1 | 3/2017 | Rao et al. | |
| 2017/0074980 A1 | 3/2017 | Adib et al. | |
| 2017/0090014 A1 | 3/2017 | Subburaj et al. | |
| 2017/0090015 A1 | 3/2017 | Breen et al. | |
| 2017/0115377 A1 | 4/2017 | Giannini et al. | |
| 2017/0131395 A1 | 5/2017 | Reynolds et al. | |
| 2017/0136289 A1* | 5/2017 | Frank .................. | A63B 21/4035 |
| 2017/0139036 A1 | 5/2017 | Nayyar et al. | |
| 2017/0141453 A1 | 5/2017 | Waelde et al. | |
| 2017/0170947 A1 | 6/2017 | Yang | |
| 2017/0176574 A1 | 6/2017 | Eswaran et al. | |
| 2017/0192847 A1 | 7/2017 | Rao et al. | |
| 2017/0201019 A1 | 7/2017 | Trotta | |
| 2017/0212597 A1 | 7/2017 | Mishra | |
| 2017/0364160 A1 | 12/2017 | Malysa et al. | |
| 2017/0368413 A1* | 12/2017 | Shavit ................ | A63B 24/0075 |
| 2018/0046255 A1 | 2/2018 | Rothera et al. | |
| 2018/0071473 A1 | 3/2018 | Trotta et al. | |
| 2018/0101239 A1 | 4/2018 | Yin et al. | |
| 2018/0345070 A1* | 12/2018 | Yakovenko ........ | A63B 22/0242 |
| 2019/0240541 A1* | 8/2019 | Denton ............ | A63B 21/00076 |

FOREIGN PATENT DOCUMENTS

| | | |
|---|---|---|
| CN | 101490578 A | 7/2009 |
| CN | 101585361 A | 11/2009 |
| CN | 102788969 A | 11/2012 |
| CN | 102967854 A | 3/2013 |
| CN | 103529444 A | 1/2014 |

(56) References Cited

FOREIGN PATENT DOCUMENTS

| | | |
|---|---|---|
| CN | 203950036 U | 11/2014 |
| DE | 102008054570 A1 | 6/2010 |
| DE | 102011100907 A1 | 1/2012 |
| DE | 102011075725 A1 | 11/2012 |
| DE | 102014118063 A1 | 7/2015 |
| GB | 2247799 A | 3/1992 |
| JP | 2001174539 A | 6/2001 |
| JP | 2004198312 A | 7/2004 |
| JP | 2006234513 A | 9/2006 |
| JP | 2008029025 A | 2/2008 |
| JP | 2008089614 A | 4/2008 |
| JP | 2009069124 A | 4/2009 |
| JP | 2011529181 A | 12/2011 |
| JP | 2012112861 A | 6/2012 |
| JP | 2013521508 A | 6/2013 |
| JP | 2014055957 A | 3/2014 |
| KR | 20090063166 A | 6/2009 |
| KR | 20140082815 A | 7/2014 |
| WO | 2007060069 A1 | 5/2007 |
| WO | 2013009473 A2 | 1/2013 |
| WO | 2016033361 A1 | 3/2016 |

OTHER PUBLICATIONS

Chen, Xiaolong et al., "Detection and Extraction of Marine Target with Micromotion via Short-Time Fractional Fourier Transform in Sparse Domain," IEEE International Conference on Signal Processing, Communications and Computing, ICSPCC, Aug. 5-8, 2016, 5 pages.

Chen, Xiaolong et al., "Detection and Extraction of Target with Micromotion in Spiky Sea Clutter via Short-Time Fractional Fourier Transform", IEEE Transactions on Geoscience and Remote Sensing, vol. 52, No. 2, Feb. 2014, pp. 1002-1018.

Chuanhua, Du, "FMCW Radar Range-Doppler Processing and Beam Formation Technology," Chinese Doctoral Dissertations & Master's Theses Full Text Database (Masters)—Information Science and Technology Series, China National Knowledge Infrastructure, ISSN 1674-0246, CN 11-9144/G, Dec. 16, 2004-Mar. 2015, 14 pages.

Deacon, Peter et al., "Frequency Modulated Continuous Wave (FMCW) Radar," Design Team 6 Technical Lecture, Nov. 9, 2011, 27 pages.

Dham, Vivek "Programming Chirp Parameters in TI Radar Devices," Application Report SWRA553, Texas Instruments, May 2017, 15 pages.

Diederichs, Kailtyn et al., "Wireless Biometric Individual Identification Utilizing Millimeter Waves", IEEE Sensors Letters, vol. 1, No. 1, IEEE Sensors Council 3500104, Feb. 2017, 4 pages.

Dooring Alert Systems, "Riders Matter," http:\\dooringalertsystems.com, printed Oct. 4, 2017, 16 pages.

Filippelli, Mario et al., "Respiratory dynamics during laughter," J Appl Physiol, (90), 1441-1446, Apr. 2001, http://iap.physiology.org/content/jap/90/4/1441.full.pdf., 6 pages.

Fox, Ben, "The Simple Technique That Could Save Cyclists' Lives," https://www.outsideonline.com/2115116/simple-technique-could-save-cyclists-lives, Sep. 19, 2016, 6 pages.

Gu, Changzhan et al., "Assessment of Human Respiration Patterns via Noncontact Sensing Using Doppler Multi-Radar System", Sensors Mar. 2015, 15(3), 6383-6398, doi: 10.3390/s150306383, 17 pages.

Guercan, Yalin "Super-resolution Algorithms for Joint Range-Azimuth-Doppler Estimation in Automotive Radars," Technische Universitet Delft, TUDelft University of Technology Challenge the Future, Jan. 25, 2017, 72 pages.

Inac, Ozgur et al., "A Phased Array RFIC with Built-In Self-Test Capabilities," IEEE Transactions on Microwave Theory and Techniques, vol. 60, No. 1, Jan. 2012, 10 pages.

Killedar, Abdulraheem "XWR1xxx Power Management Optimizations—Low Cost LC Filter Solution," Application Report SWRA577, Texas Instruments, Oct. 2017, 19 pages.

Kizhakkel, V., "Pulsed Radar Target Recognition Based on Micro-Doppler Signatures Using Wavelet Analysis", A Thesis, Graduate Program in Electrical and Computer Engineering, Ohio State University, Jan. 2013-May 2013, 118 pages.

Kuehnke, Lutz, "Phased Array Calibration Procedures Based on Measured Element Patterns," 2001 Eleventh International Conference on Antennas and Propagation, IEEE Conf., Publ. No. 480, Apr. 17-20, 2001, 4 pages.

Lim, Soo-Chul et al., "Expansion of Smartwatch Touch Interface from Touchscreen to Around Device Interface Using Infrared Line Image Sensors," Sensors 2015, ISSN 1424-8220, vol. 15, 16642-16653, doi:10.3390/s150716642, www.mdpi.com/journal/sensors, Jul. 15, 2009, 12 pages.

Lin, Jau-Jr et al., "Design of an FMCW radar baseband signal processing system for automotive application," SpringerPlus a SpringerOpen Journal, (2016) 5:42, http://creativecommons.org/licenses/by/4.0/, DOI 10.1186/s40064-015-1583-5; Jan. 2016, 16 pages.

Microwave Journal Frequency Matters, "Single-Chip 24 GHz Radar Front End," Infineon Technologies AG, www.microwavejournal.com/articles/print/21553-single-chip-24-ghz-radar-front-end, Feb. 13, 2014, 2 pages.

Qadir, Shahida G., et al., "Focused ISAR Imaging of Rotating Target in Far-Field Compact Range Anechoic chamber," 14th International Conference on Aerospace Sciences & Aviation Technology, ASAT-14-241-IP, May 24-26, 2011, 7 pages.

Richards, Mark A., "Fundamentals of Radar Signal Processing," McGraw Hill Electronic Engineering, ISBN: 0-07-144474-2, Jun. 2005, 93 pages.

Schroff, Florian et al., "FaceNet: A Unified Embedding for Face Recognition and Clustering," CVF, CVPR2015, IEEE Computer Society Conference on Computer Vision and Pattern Recognition; Mar. 12, 2015, pp. 815-823.

Simon, W., et al., "Highly Integrated KA-Band Tx Frontend Module Including 8×8 Antenna Array," IMST GmbH, Germany, Asia Pacific Microwave Conference, Dec. 7-10, 2009, 63 pages.

Suleymanov, Suleyman, "Design and Implementation of an FMCW Radar Signal Processing Module for Automotive Applications," Master Thesis, University of Twente, Aug. 31, 2016, 61 pages.

Thayaparan, T. et al., "Intelligent target recognition using micro-Doppler radar signatures," Defence R&D Canada, Radar Sensor Technology III, Proc. of SPIE, vol. 7308, 730817, Dec. 9, 2009, 11 pages.

Thayaparan, T. et al., "Micro-Doppler Radar Signatures for Intelligent Target Recognition," Defence Research and Development Canada, Technical Memorandum, DRDC Ottawa TM 2004-170, Sep. 2004, 73 pages.

Wilder, Carol N., et al., "Respiratory patterns in infant cry," Canada Journal of Speech, Human Communication Winter, 1974-75, http://cjslpa.ca/files/1974_HumComm_Vol_01/No_03_2-60/Wilder_Baken_HumComm_1974.pdf, pp. 18-34.

Xin, Qin et al., "Signal Processing for Digital Beamforming FMCW SAR," Hindawi Publishing Corporation, Mathematical Problems in Engineering, vol. 2014, Article ID 859890, http://dx.doi.org/10.1155/2014/859890, Apr. 15, 2014, 11 pages.

* cited by examiner

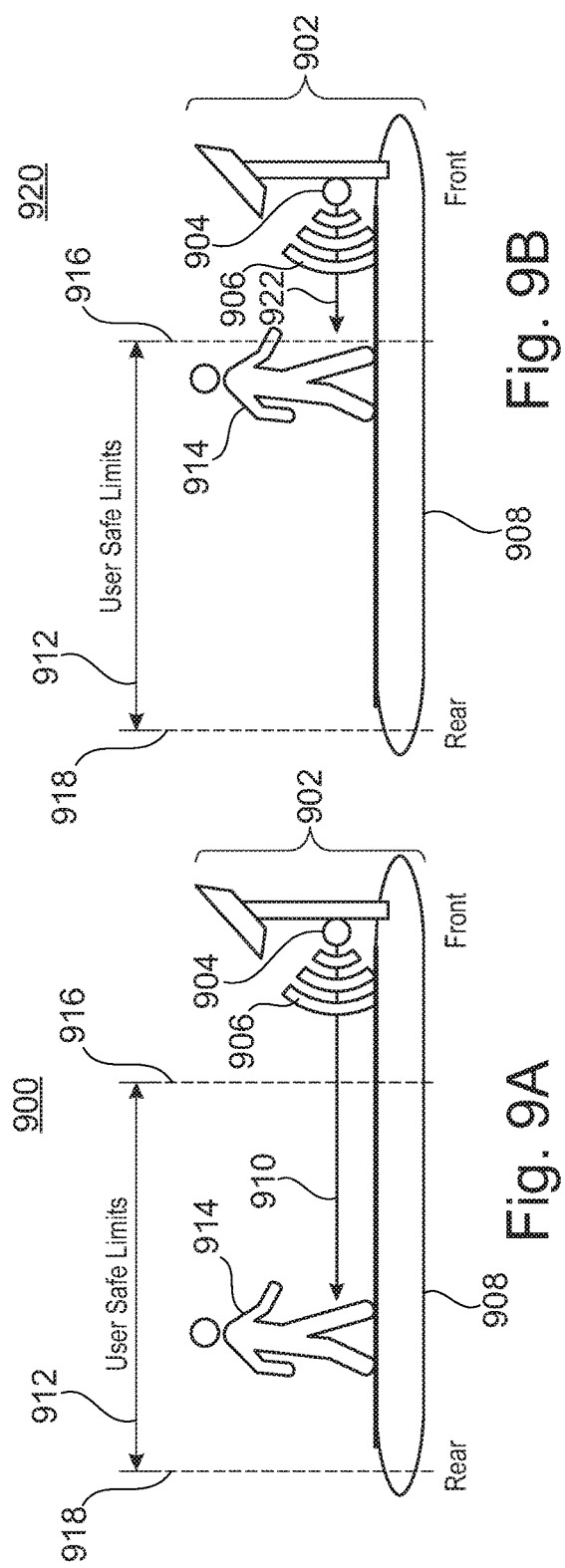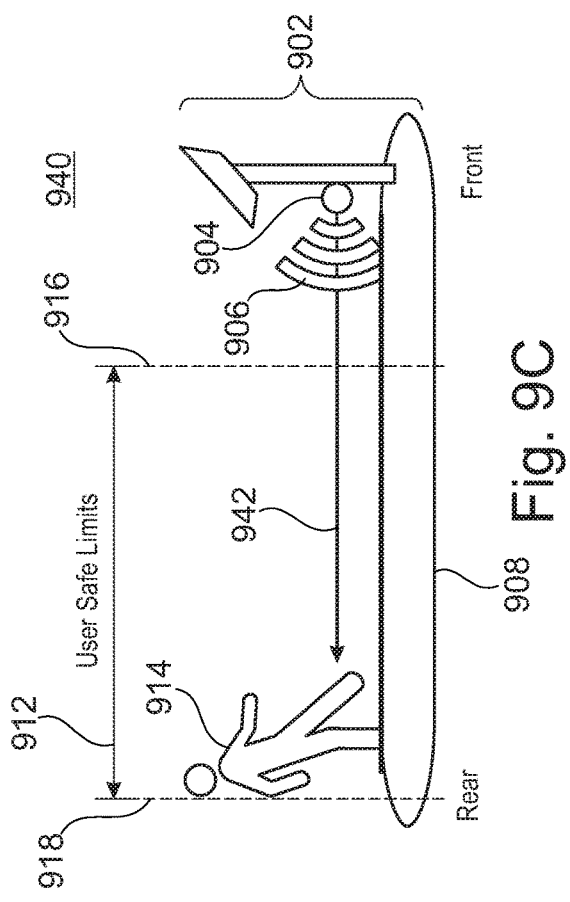

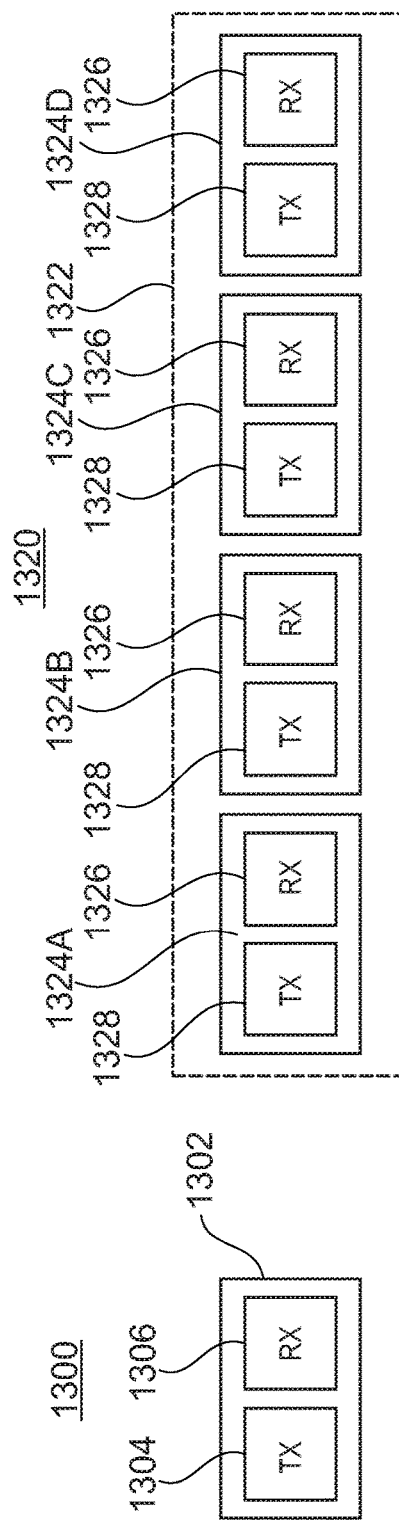
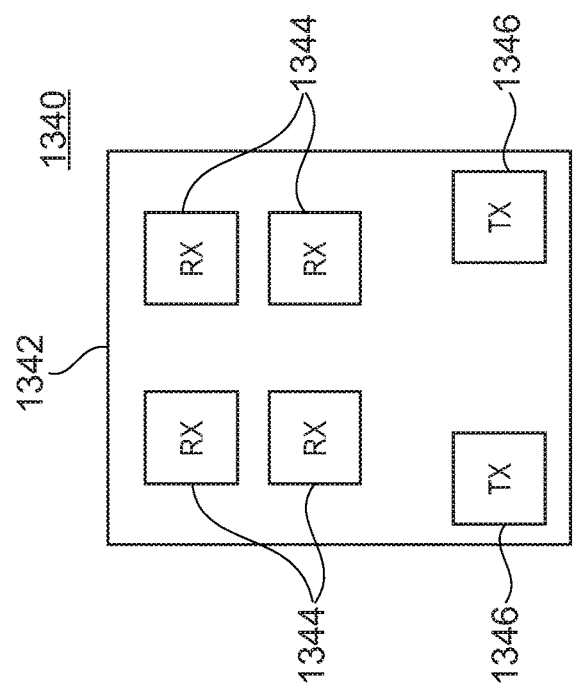
Fig. 13A
Fig. 13B
Fig. 13C

SYSTEM AND METHOD FOR CONTACTLESS SENSING ON A TREADMILL

TECHNICAL FIELD

The present invention relates generally to a system and method for contactless sensing on a treadmill, and, in particular embodiments, to a system and method for sensing a treadmill user's vital statistics and movement remotely while the user exercises on the treadmill.

BACKGROUND

Generally, treadmills measure the distance a user travels indirectly, by measuring the speed of the treadmill belt, and integrating the speed over a particular time. The number of calories burned by a user is estimated based on the distance the treadmill belt travels at a particular speed and/or treadmill belt slope.

More sophisticated treadmills may provide monitoring of user vital statistics, such as a heart rate, using a contact sensor such as a grip sensor, or wireless heart rate monitor worn by the user. However, grip sensors require a user to hold a conductive region of the treadmill for a significant time to permit the sensor to read electrical signals in the user's hands. Similarly, wireless heart rate sensor must be worn by a user with a sensor on the wireless device in contact with the user to acquire the heart rate. Additionally, the contact-type vital sensors are limited to sensing heart rate, and cannot provide information on other vital statistics.

SUMMARY

Thus, an embodiment treadmill includes a belt, a display, a first sensor having first transmission circuitry for transmitting a first radar beam over the belt and first reception circuitry for detecting a first reflected signal that is a reflection of the first radar beam from a user on the belt, a processor connected to the first sensor, the belt and the display, and a non-transitory computer-readable storage medium storing a program to be executed by the processor. The program includes instructions for determining, according to the first reflected signal, first data associated with a vital sign of the user and displaying, according to the first data, the vital sign on the display.

An embodiment method includes receiving, by a first sensor of a treadmill, a first reflected signal that is a first reflection of a first radar beam reflected from a user on a belt of the treadmill, receiving, by a second sensor of a treadmill, a second reflected signal that is a second reflection of a second radar beam reflected from the user, generating, according to the first reflected signal, first data associated at least one of a gesture of the user or a position of the user on the belt, generating, according to the second reflected signal, second data associated with a vital sign of the user, controlling at least one of the belt and a display of the treadmill according to the first data and displaying, according to the second data, the vital sign on the display.

An embodiment method includes moving a belt of a treadmill, transmitting a first radar beam over the belt toward a user on the belt while the belt is moving, detecting a first reflected signal that is a first reflection of the first radar beam from the user, generating, according to the first reflected signal, first data associated with a vital sign of the user, and displaying, according to the first data, the vital sign on a display of the treadmill.

BRIEF DESCRIPTION OF THE DRAWINGS

For a more complete understanding of the present invention, and the advantages thereof, reference is now made to the following descriptions taken in conjunction with the accompanying drawings, in which:

FIGS. 9A through 9C illustrate various scenarios for control of a treadmill based on user positioning according to some embodiments;

FIGS. 13A through 13C illustrates radar sensor arrangements according to some embodiments.

DETAILED DESCRIPTION OF ILLUSTRATIVE EMBODIMENTS

Figure 1:
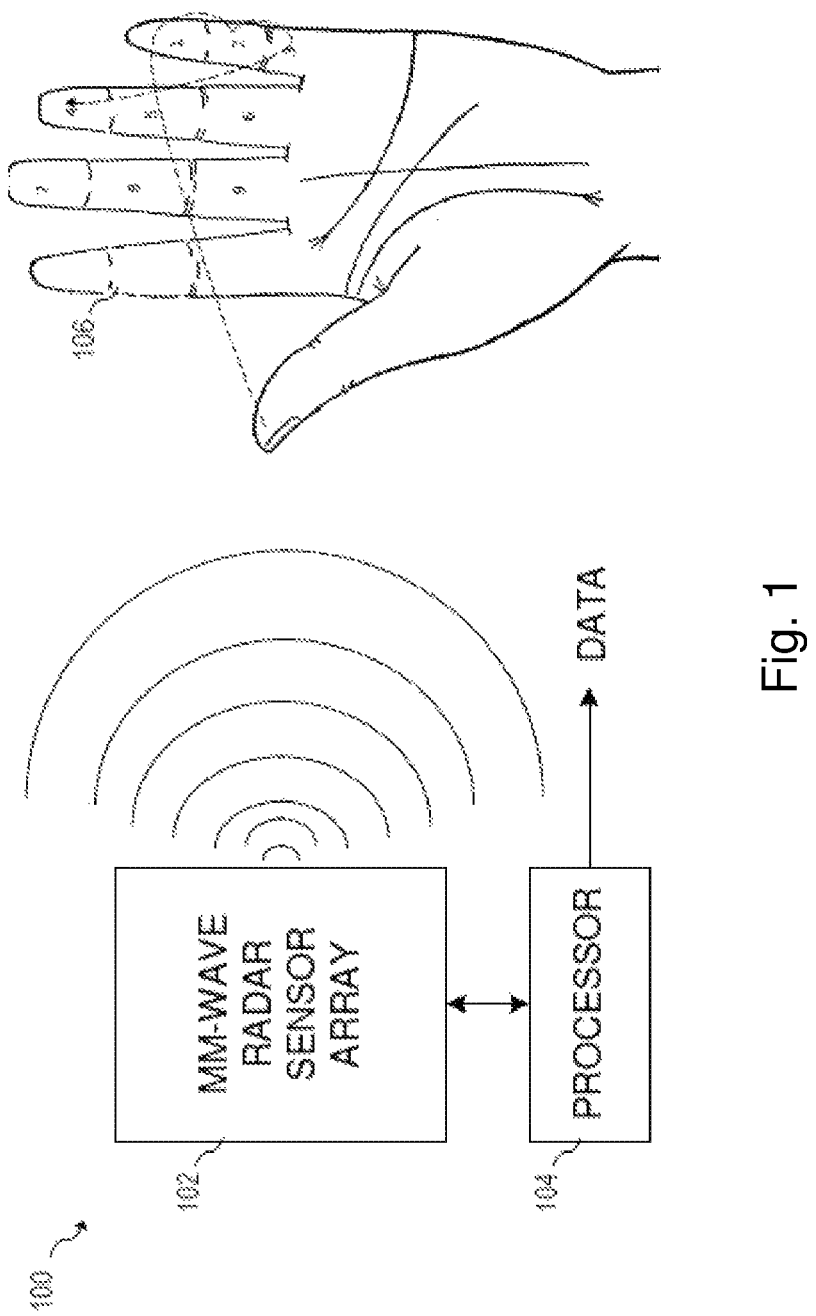
FIG. 1 illustrates an embodiment vital signal measurement system.

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

Embodiments of the present invention are described in a specific context, including a system and method for contactless sensing of user characteristics for a treadmill, and in particular, to sensing of a treadmill user's characteristics using one or more millimeter-wave radar sensors. The invention may also be applied to other RF-based systems and applications that perform detection of user characteristics.

Applications in the millimeter-wave frequency regime have gained significant interest in the past few years due to the rapid advancement in low cost semiconductor technologies such as silicon germanium (SiGe) and fine geometry complementary metal-oxide semiconductor (CMOS) processes. Availability of high-speed bipolar and metal-oxide semiconductor (MOS) transistors has led to a growing demand for integrated circuits for millimeter-wave applications at 60 GHz, 77 GHz and 80 GHz and also beyond 100 GHz. Such applications include, for example, automotive radar systems and multi-gigabit communication systems.

In some radar systems, the distance between the radar and a target is determined by transmitting a frequency modulated signal, receiving a reflection of the frequency modulated signal, and determining a distance based on a time delay and/or frequency difference between the transmission and reception of the frequency modulated signal. Accordingly, some radar systems include a transmit antenna to transmit the radio frequency (RF) signal, a receive antenna to receive the RF, as well as the associated RF circuitry used to generate the transmitted signal and to receive the RF signal. In some cases, multiple antennas may be used to implement directional beams using phased array techniques. A multiple input multiple output (MIMO) configuration with multiple chipsets can be used to perform coherent and non-coherent signal processing, as well.

In some embodiments, one or more millimeter-wave based sensors are used to detect the vital signs, gestures, and position of a user or a user's body parts in a treadmill active area. For example, a sensor, such as a millimeter-wave based sensor, may use radar measurements to detect user characteristics such as vital signs, including heart rate and respiration. The same sensor, or a different sensor, may also be used to detect user characteristics such as user gestures, including head gestures, hand or arm gestures, or the like. Additionally, sensors may be used to detect a user's position within the treadmill active area, and detect the positioning of the user's body, legs, head, arms, or the like for use in, for example, posture analysis. During operation, the millimeter-wave radar sensor first performs a coarse measurement using macro-Doppler techniques to determine the presence of moving and non-moving objects. In some embodiments, non-vital motion is categorized using macro-Doppler techniques. Next, the millimeter-wave radar system performs a series of more targeted measurements of the detected objects using vital -Doppler techniques to determine whether these detected objects exhibit a heart-rate and respiration within the expected range of a human being. Based on these measurements, an embodiment system can determine the heart rate and respiration rate of a treadmill user. In addition, embodiment systems can use millimeter-wave measurements to classify the identity of detected objects. Embodiment radar signal processing techniques can also be used to distinguish human beings from other moving objects such as animals, robots, machinery and the like in order to filter out unwanted signals.

Macro-doppler signals due to a user running or jogging on a treadmill may overshadow the doppler signals from vital signs or gestures, making such micro-doppler signals undetectable. Embodiments of a contactless treadmill with macro-doppler sensing performed in separate observation windows are provided below. Embodiments of the contactless sensing treadmill, use integrated millimeter-wave radar sensors in a treadmill for gesture sensing to allow for gesture control for the user interface, detection of leg movement for determination of step count, precise distance covered and calories burned, extraction of heart rate and breathing rate for analyzing vital behavior during exercise, extraction of running behavior for pose assessment and correction, and automatic hands-free control of the treadmill speed and elevation to optimize the exercise and provide additional control during exercise.

In some embodiments, data from macro-doppler observation windows may be used to predict the doppler in the micro-doppler observation window. Thus, the treadmill may automatically determine the user's velocity and position, along with vital signs or gesture sensing. This permits automatic hands-free control of treadmill based on position and velocity of the user. Additionally, gesture sensing may be used to control the treadmill interface for user operations to, for example, control an interactive display, and perform emergency stops of the treadmill. Micro-doppler movement signals may be extracted from the same sensor that determines macro-doppler movement and may be used to precisely calculate the speed, number of steps and distance covered.

Various embodiments of a contactless sensing treadmill may include a multiple sensor configuration, with each separate sensor used for specific operations, or may include a single sensor configuration that enables interleaved modes between macro-doppler, micro-doppler and gesture extraction.

In embodiments of the present invention, a millimeter-wave based radar sensor is mounted on a treadmill for measuring vital signal information such as pulse rate and respiration. In various embodiments, the relevant vital signal is determined by using high response "range gate" measurements that may be determined, for example, by taking a fast Fourier transform (FFT) of downconverted frequency modulated continuous wave (FMCW) measurements from the millimeter-wave based radar sensor. These range gate measurements are then filtered to determine the relevant vital signal. Such filtering may be adaptively calibrated to compensate for irregularities in the physical coupling between the millimeter-wave based radar sensor and the body being measured. In some embodiments, the motion of the body being measured with respect to the millimeter-wave based radar sensor is compensated for by tracking shifts in the high response range gates and stitching together measurements from multiple range gates to form the basis for the vital signal measurement.

Advantages of embodiment vital signal sensing systems may include the ability to perform accurate vital signal measurements in the presence of relative motion between the millimeter-wave based radar sensor and the body being measured, while avoiding the need for a user being measured to physically contact the treadmill. Such advantages are particularly relevant for vital sensing applications in which heartbeat and/or respiration is measured on a human being in motion without requiring changes in, or interruption of, the user's exercise.

FIG. 1A illustrates a block diagram of radar-based vital signal measuring system 100. As shown, radar-based vital signal measuring system wo includes a millimeter-wave radar sensor 102, and a processor 104 that controls the operation of millimeter-wave radar sensor 102 and performs various radar signal processing operations on the data produced by millimeter-wave radar sensor 102. During operation, millimeter-wave radar sensor 102 transmits millimeter-wave RF signals that are reflected by object 106. While object 106 is depicted as a human hand, it should be understood that object 106 may be any body from which a vital signal is to be measured. The reflected signals are received by millimeter-wave radar sensor 102, converted to a digital representation, and processed by processor 104 to determine, for example, a vital signal produced by object 106, such as a pulse rate. The result of this processing produces various data (represented by signal DATA) indicative of the measured vital signals.

Figure 2A:
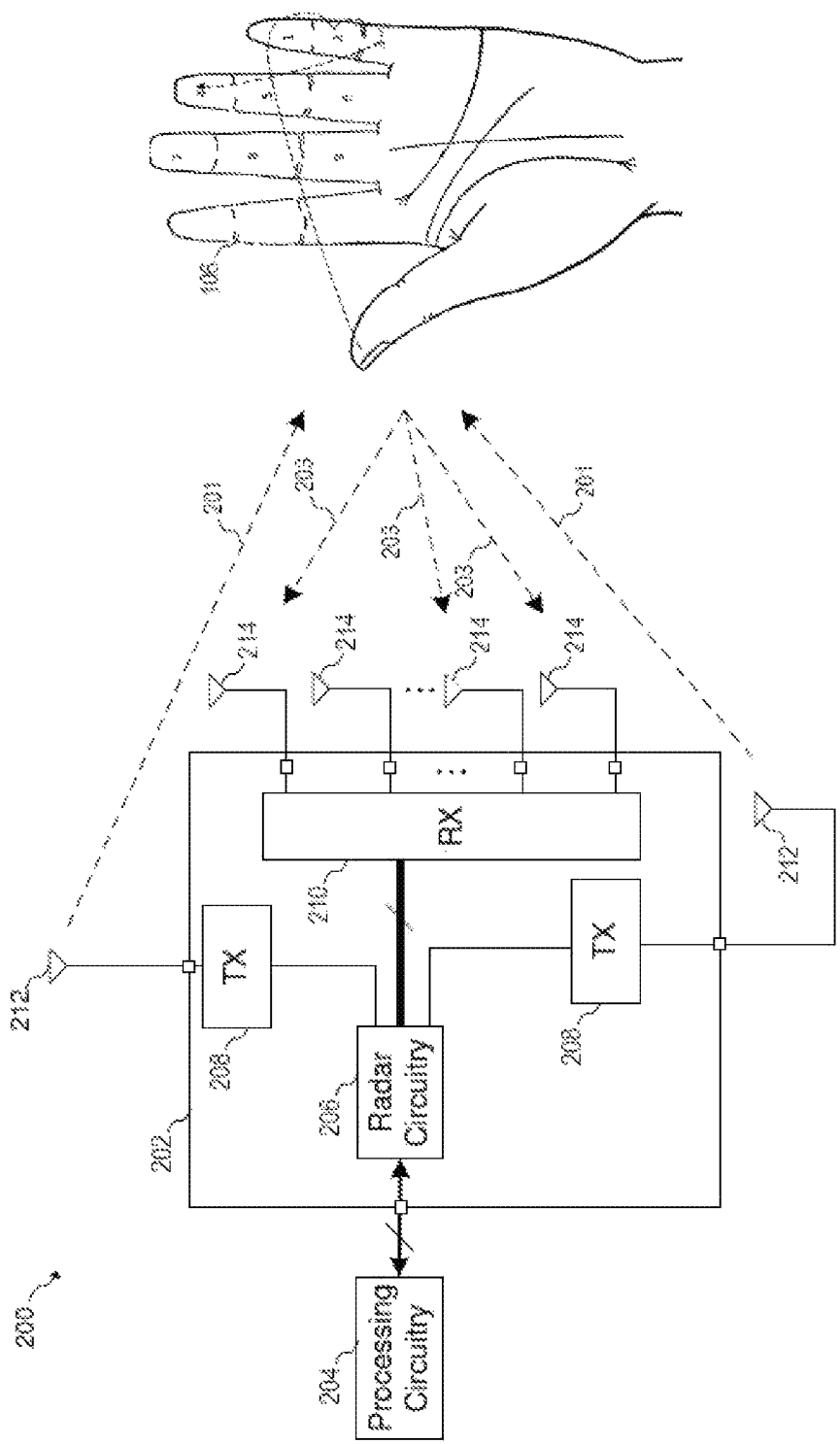
FIG. 2A illustrates a block diagram of an embodiment millimeter-wave radar sensor.

FIG. 2A illustrates a block diagram of a millimeter-wave radar sensor system 200 that may be used to implement millimeter-wave radar sensor circuits in the various disclosed embodiments. Millimeter-wave radar sensor system 200 includes millimeter-wave radar sensor circuit 202 and processing circuitry 204. Embodiment millimeter-wave radar sensor circuits may be implemented, for example, using a two-dimensional millimeter-wave phase-array radar that performs measurements on object 106. The millimeter-wave phase-array radar transmits and receives signals in the 20 GHz to 122 GHz range. Frequencies outside of this range may also be used. In some embodiments, millimeter-wave radar sensor circuit 202 operates as a frequency modulated continuous wave (FMCW) or interferometric radar sensor having multiple transmit and receive channels. Alternatively, other types of radar systems may be used such as pulse radar, Multiple Continuous Frequency Wave (MCFW), and nonlinear frequency modulation (NLFM) to implement millimeter-wave radar sensor circuit 202.

Millimeter-wave radar sensor circuit 202 transmits and receives radio signals for detecting and determining positioning, movement, distance and vital signals of object 106. For example, millimeter-wave radar sensor circuit 202 transmits incident RF signals 201 and receives RF signals 203 that are a reflection of the incident RF signals from object 106. The received reflected RF signals 203 are downconverted by millimeter-wave radar sensor circuit 202 to determine, for example, beat frequency signals. These beat frequency signals may be used to determine information such as the location and motion of object 106. In the specific example of FMCW radar, the beat frequency is proportional to the distance between millimeter-wave radar sensor circuit 202 and the object being sensed.

In various embodiments, millimeter-wave radar sensor circuit 202 is configured to transmit incident RF signals 201 toward object 106 via transmit antennas 212 and to receive reflected RF signals 203 from object 106 via receive antennas 214. Millimeter-wave radar sensor circuit 202 includes transmitter front-end circuits 208 coupled to transmit antennas 212 and receiver front-end circuit 210 coupled to receive antennas 214.

During operation, transmitter front-end circuits 208 may transmit RF signals toward object 106 simultaneously or individually using beamforming depending on the phase of operation. While two transmitter front-end circuits 208 are depicted in FIG. 2A, it should be appreciated that millimeter-wave radar sensor circuit 202 may include less than or greater than two transmitter front-end circuits 208. Thus, in various embodiments, the number of transmitters can be extended to n×m. Each transmitter front-end circuit 208 includes circuitry configured to produce the incident RF signals. Such circuitry may include, for example, RF oscillators, upconverting mixers, RF amplifiers, variable gain amplifiers, filters, transformers, power splitters, and other types of circuits.

Receiver front-end circuit 210 receives and processes the reflected RF signals from object 106. As shown in FIG. 2A, receiver front-end circuit 210 is configured to be coupled to four receive antennas 214, which may be configured, for example, as a 2×2 antenna array. In alternative embodiments, receiver front-end circuit 210 may be configured to be coupled to greater or fewer than four antennas, with the resulting antenna array being of various n x m dimensions depending on the specific embodiment and its specifications. Receiver front-end circuit 210 may include, for example, RF oscillators, upconverting mixers, RF amplifiers, variable gain amplifiers, filters, transformers, power combiners and other types of circuits.

Radar circuitry 206 provides signals to be transmitted to transmitter front-end circuits 208, receives signals from receiver front-end circuit 210, and may be configured to control the operation of millimeter-wave radar sensor circuit 202. In some embodiments, radar circuitry 206 includes, but is not limited to, frequency synthesis circuitry, upconversion and downconversion circuitry, variable gain amplifiers, analog-to-digital converters, digital-to-analog converters, digital signal processing circuitry for baseband signals, bias generation circuits, and voltage regulators.

Radar circuitry 206 may receive a baseband radar signal from processing circuitry 204 and control a frequency of an RF oscillator based on the received baseband signal. In some embodiments, this received baseband signal may represent a FMCW frequency chirp to be transmitted. Radar circuitry 206 may adjust the frequency of the RF oscillator by applying a signal proportional to the received baseband signal to a frequency control input of a phase locked loop. Alternatively, the baseband signal received from processing circuitry 204 may be upconverted using one or more mixers. Radar circuitry 206 may transmit and digitize baseband signals via a digital bus (e.g., a USB bus), transmit and receive analog signals via an analog signal path, and/or transmit and/or receive a combination of analog and digital signals to and from processing circuitry 204.

Processing circuitry 204 acquires baseband signals provided by radar circuitry 206 and formats the acquired baseband signals for transmission to an embodiment signal processing unit. These acquired baseband signals may represent beat frequencies, for example. In some embodiments, processing circuitry 204 includes a bus interface (not shown) for transferring data to other components within, for example, a contactless sensor system for a treadmill. Optionally, processing circuitry 204 may also perform signal processing steps used by the contactless sensing treadmill system such as a fast Fourier transform (FFT), a short-time Fourier transform (STFT), macro-Doppler analysis, micro-Doppler analysis, vital sign analysis, object classification, machine learning, and the like. In addition to processing the acquired baseband signals, processing circuitry 204 may also control aspects of millimeter-wave radar sensor circuit 202, such as controlling the transmissions produced by millimeter-wave radar sensor circuit 202.

The various components of millimeter-wave radar sensor system 200 may be partitioned in various ways. For example, millimeter-wave radar sensor circuit 202 may be implemented on one or more RF integrated circuits (RFICs), antennas 212 and 214 may be disposed on a circuit board, and processing circuitry 204 may be implemented using a processor, a microprocessor, a digital signal processor and/or a custom logic circuit disposed on one or more integrated circuits/semiconductor substrates. Processing circuitry 204 may include a processor that executes instructions in an executable program stored in a non-transitory computer readable storage medium, such as a memory, to perform the functions of processing circuitry 204. In some embodiments, however, all or part of the functionality of processing circuitry 204 may be incorporated on the same integrated circuit/semiconductor substrate on which millimeter-wave radar sensor circuit 202 is disposed.

In some embodiments, some or all portions of millimeter-wave radar sensor circuit 202 may be implemented in a package that contains transmit antennas 212, receive antennas 214, transmitter front-end circuits 208, receiver front-end circuit 210, and/or radar circuitry 206. In some embodiments, millimeter-wave radar sensor circuit 202 may be implemented as one or more integrated circuits disposed on a circuit board, and transmit antennas 212 and receive antennas 214 may be implemented on the circuit board adjacent to the integrated circuits. In some embodiments, transmitter front-end circuits 208, receiver front-end circuit 210, and radar circuitry 206 are formed on a same radar front-end integrated circuit (IC) die. Transmit antennas 212 and receive antennas 214 may be part of the radar front-end IC die, or may be implemented as separate antennas disposed over or adjacent to the radar front-end IC die. The radar front-end IC die may further include conductive layers, such as redistribution layers (RDLs), used for routing and/or for the implementation of various passive or active devices of millimeter-wave radar sensor circuit 202. In an embodiment, transmit antennas 212 and receive antennas 214 may be implemented using the RDLs of the radar front-end IC die.

Figure 2C:
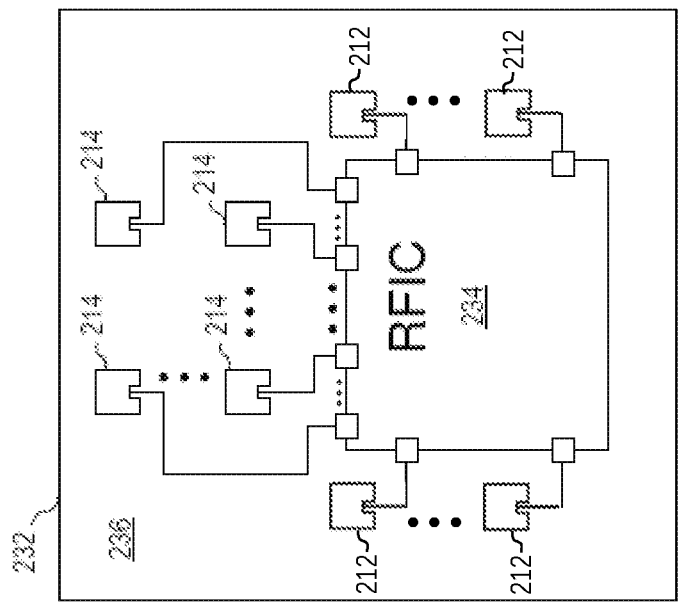
FIGS. 2B and 2C illustrate plan views of embodiment millimeter-wave radar sensor circuits.
Figure 2B:
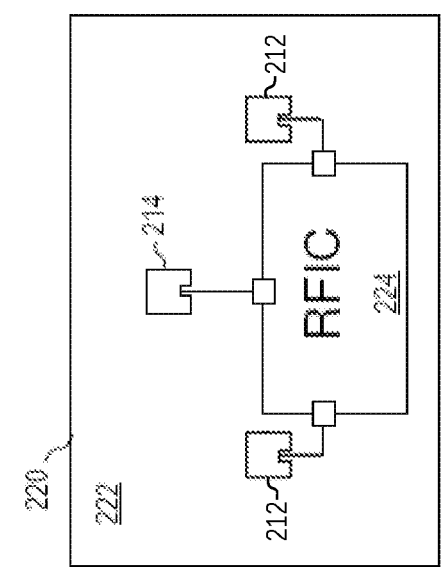

FIG. 2B illustrates a plan view of millimeter-wave radar sensor circuit 220 that may be used to implement millimeter-wave radar sensor circuit 202. As shown, millimeter-wave radar sensor circuit 220 is implemented as an RFIC 224 coupled to transmit antennas 212 and receive antenna 214 implemented as patch antennas disposed on or within substrate 222. In some embodiments, substrate 222 may be implemented using a circuit board on which millimeter-wave radar sensor circuit 202 is disposed and on which transmit antennas 212 and receive antennas 214 are implemented using conductive layers of the circuit board. Alternatively, substrate 222 represents a wafer substrate on which one or more RDLs are disposed and on which transmit antennas 212 and receive antennas 214 are implemented using conductive layers on the one or more RDLs.

FIG. 2C illustrates a plan view of millimeter-wave radar sensor circuit 232 that includes an array of transmit antennas 212 and an array of receive antennas 214 coupled to RFIC 234 disposed on substrate 236. In various embodiments, transmit antennas 212 may form an array of m antennas and receive antennas 214 may form an array of n antennas. Each of the m transmit antennas 212 is coupled to a corresponding pin on RFIC 234 and coupled to a corresponding transmit circuit within RFIC 234; and each of the n receive antennas 214 is coupled to a corresponding pin on RFIC 234 and coupled to a corresponding receive circuit within RFIC 234. In various embodiments, the array of transmit antennas 212 and the array of receive antennas 214 may be implemented as a uniform array or a linear array of any dimension. It should be appreciated that the implementations of FIGS. 2B and 2C are just two examples of the many ways that embodiment millimeter-wave radar sensor circuits could be implemented.

Figure 2D:
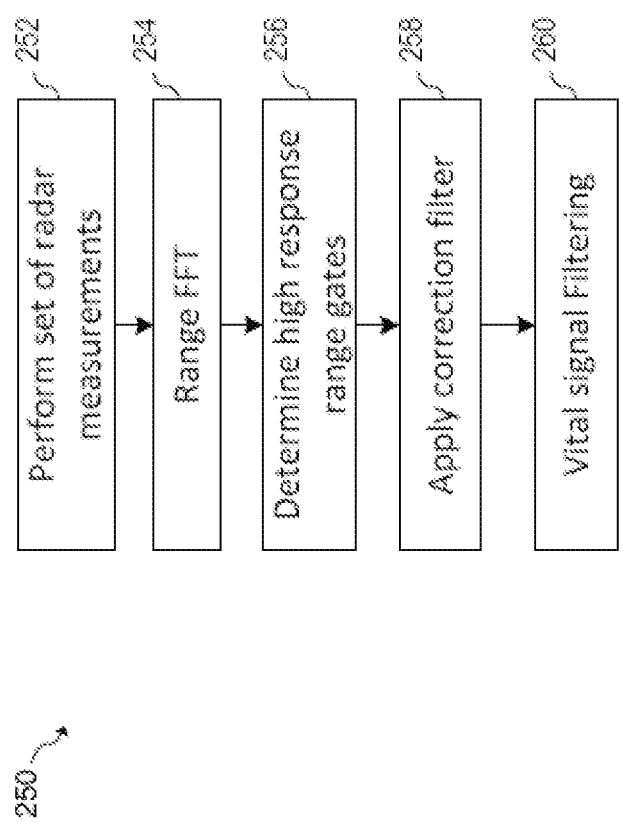
FIG. 2D illustrates a block diagram of an embodiment vital signal sensing method.

FIG. 2D illustrates a method 250 of performing vital signal measurement that may be used in conjunction with an embodiment millimeter-wave radar sensor circuit such as millimeter-wave radar sensor circuit 202, 220, or 232 described above with respect to FIGS. 2A, 2B and 2C. In block 252, the millimeter-wave sensor circuit performs a set of radar measurements, such as FMCW or interferometric radar measurements. In block 254 an FFT is taken of the baseband representation of these measurements, which are in the form of beat frequencies. Such an FFT may be referred to as a "range FFT" because each bin of the resulting FFT represents energy reflected by an object at a particular range or distance. In alternative embodiments, other transforms may be used besides an FFT, such as a discrete Fourier transform (DFT), a discrete cosine transform (DCT), or other transform types known in the art. In block 256, the highest amplitude FFT bins or "range gates" are determined. These high response range gates represent the distance to the largest objects in the range of the millimeter-wave radar sensor. Thus, in various embodiments in which the monitored object is a portion of the human body that includes arteries or portions of the body that move during respiration, the motion of these high response range gates may contain information related to the monitored object's heart rate or respiration rate. In some embodiments, determining the high response range gates includes determining which range gates of a first set of range gate measurements have a highest peak-to-average ratio.

In block 258, a correction filter is applied to the high response range gates. This correction filter may provide equalization and/or compensate for losses or distortion in the physical coupling between the millimeter-wave radar sensor and the target. In some embodiments, this correction filter is an adaptive filter, such as an adaptive finite impulse response (FIR) filter, that is calibrated according to a particular use case. Another correction filter may be calibrated to correct for the coupling between the millimeter-wave radar sensor mounted in a chest strap or and the user's chest. The correction filter may be calibrated to correct for the coupling between the millimeter-wave radar sensor and other mounting or use scenarios. In some embodiments, this correction filter may be calibrated using an adaptation algorithm during the manufacture of the vital signal sensing device and/or during a user calibration of the vital signal sensing device, as will be described below. In some embodiments, an applicable correction filter (or correction filter coefficients) may be selected based on the particular use case. In block 260, the output of the correction filter is further filtered by a vital signal filter to extract vital signal information such as heart beat and respiration signals.

Figure 3:
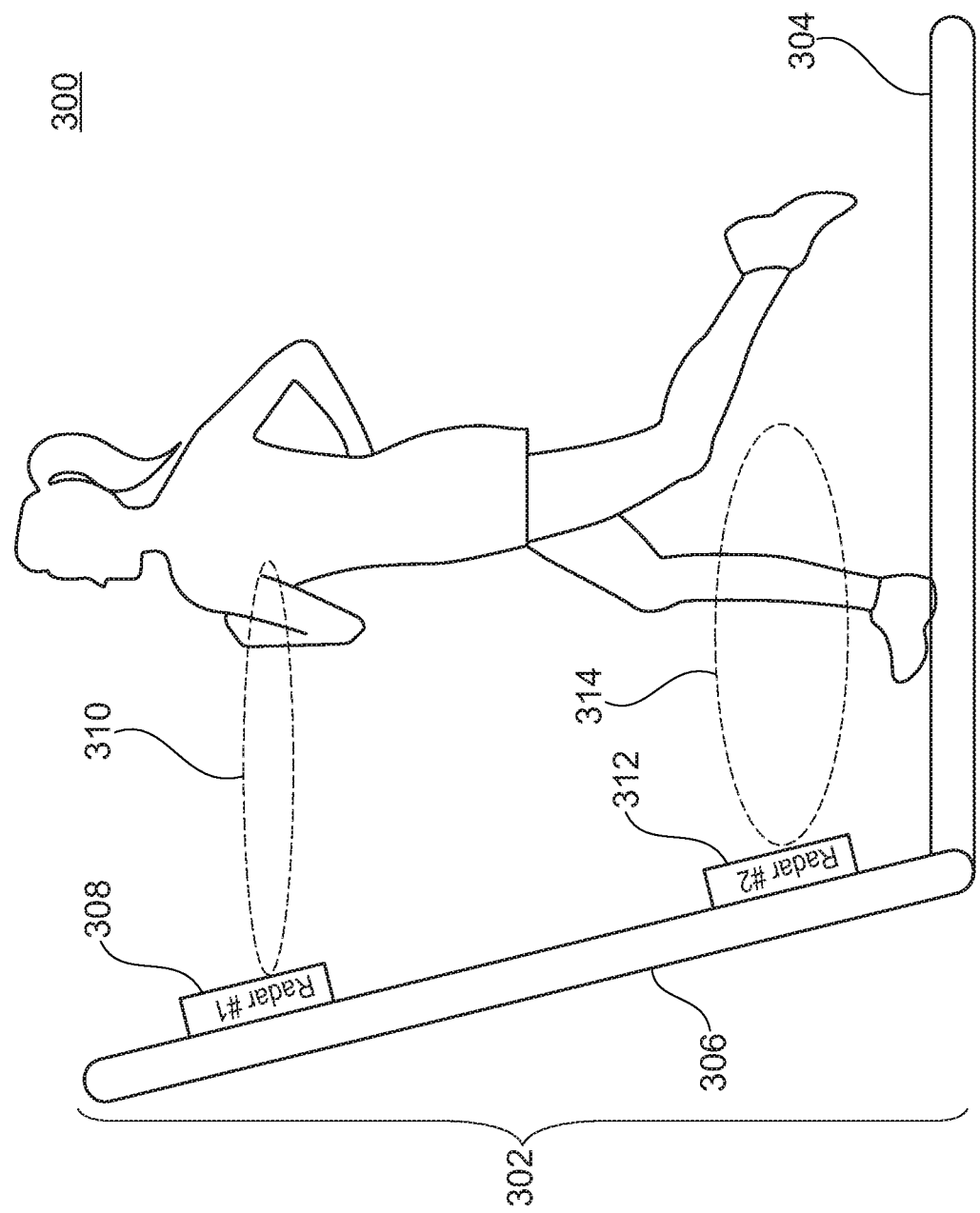
FIG. 3 illustrates a contactless sensing treadmill system according to some embodiments.

FIG. 3 illustrates a contactless sensing treadmill system 300 according to some embodiments. In some embodiments, the system is a treadmill 302 having a belt 304 that moves, permitting a user to run on the treadmill 302. A podium or support 306 supports a first radar sensor 308 and a second radar sensor 312. The treadmill 302 moves the belt 304 and measures user characteristics while the user is on the moving belt to provide exercise related data to the user and to further provide control of the treadmill without the user needing to contact the treadmill with their hands. Thus, the treadmill provides a fully integrated user experience in a contactless manner while allowing the user to exercise in a natural form.

The first radar sensor 308 transmits a narrow beam 310 over the belt 304 toward a user's torso and head, and receives signals used to monitor heart rate and breathing rate for a user on the belt 304. The first radar sensor 308 may switch between an interferometric mode and a FMCW mode to estimate vital doppler signals.

In some embodiments, the first radar sensor 308 may also be used for gesture detection, such as hand or head gestures. For example, the first radar sensor 308 may be used to control a television, display radio, or the like in response to head gestures. Thus, if a user is watching TV and wants to switch channels while running, the first radar sensor 308 may detect the user turning their head left or right, and will change the channel or adjust the display or radio appropriately. Additionally, a specific gesture such as the user turning their head, raising both hands, making a fist, or the like may be treated as an emergency stop instruction to the treadmill The second radar sensor 312 uses a second beam 314 to measure range & doppler from leg movement. In some embodiments, the second radar sensor 312 may provide feedback to the treadmill based on user range. The treadmill 302 may use the feedback from the second radar sensor 312, along with the sensed vitals from the first radar sensor 308, to determine whether to change the speed or incline of the belt 304. For example, if the user heart rate exceeds a heart rate threshold, and the breathing rate exceeds a breathing rate threshold, which may indicate that the user is panting, the treadmill 302 may slow down the belt 304 automatically, or lower the slope of the belt 304. Similarly, if a user's hear rate and breathing rate are below the respective thresholds, or below second or lower thresholds, the treadmill 302 may adjust the speed or incline of the belt 304 based on the position of the user, speeding up the belt or increasing the slope if the user is near the front of the belt.

Additionally, the first radar sensor 308 or second radar sensor 312 may be used to detect and analyze the posture of the user while moving on the belt 304. For example, the micro-doppler extracted from the second radar sensor 312 may be fed into a machine learning pipeline to analyze the user's posture, and the treadmill may provide the feedback or warnings on display to assist in avoiding injury to the user. The treadmill 302 may also provide additional information to a user, such as distance travelled, calories burned, or the like. For example, a velocity of a user or a distance travelled may be extracted from the second radar sensor 312 by measuring movement and position of a user's legs. Similarly, a heart rate may be extracted from the first radar sensor 308, and the distance and/or velocity extracted from the second radar sensor 312 to compute the calories burned. In some embodiments, the treadmill speed, slope and acceleration may also be used to compute the calories burned.

Figure 4:
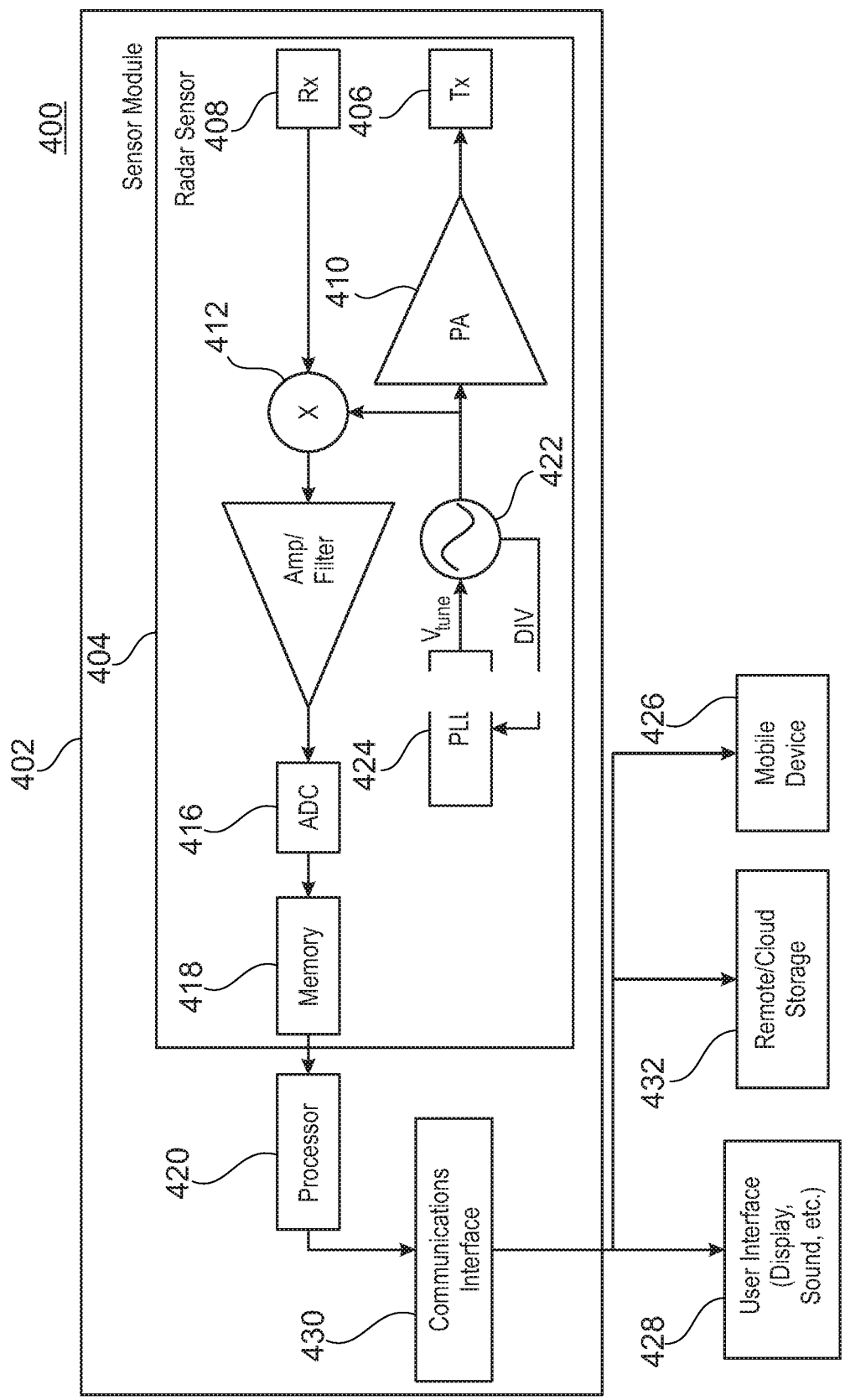
FIG. 4 illustrates a sensor system for a contactless sensing treadmill according to some embodiments.

FIG. 4 illustrates a sensor system 400 for a contactless sensing treadmill according to some embodiments. The sensor system 400 may have one or more sensor modules 402, with each sensor module 402 having one or more radar sensors 404. Each radar sensor 404 may act independently and provide a signal for processing by a processor 420 of the sensor module 402. A radar sensor 404 has one or more transmitters (Tx) 406. A phase locked loop (PLL) 424 circuit element generates a reference signal ($V_{tune}$) that controls the output of a voltage controlled oscillator (VCO) 422. The VCO 422 feeds back a reference signal (DIV) to the PLL 424 and further provides an output signal to a power amplifier (PA) 410. The PA amplifies the signal from the VCO 422, and the amplified signal is provided to the transmitters 406, which transmit the amplified signal as one or more millimeter-wave radar beams.

Reflected radar energy from transmissions of the transmitters 406 are received by one or more receivers (Rx) 408. The receivers 408 may detect crosstalk noise such as signals transmitted directly from the transmitters 406 in combination with signals reflected from a target such as a user on a treadmill. The receivers 408 generate a receiver electrical signal from the received radar signal, and send the receiver electrical signal to a mixer 412. The mixer 412 may filter out the crosstalk noise using a reference signal received from the output of the VCO 422 to generate a reflection signal. The reflection signal is provided to an amplifier/filter 414, which may perform additional filtering or amplification on the reflection signal, for example, by amplifying or attenuating one or more portions, frequencies, or bands of the reflection signal. The amplifier/filter 414 provides the filtered signal to an analog-to-digital converter (ADC) 416 where the filtered signal is digitized and stored as digitized signal data in a memory 418 for processing by the processor 420.

The processor 420 is, in some embodiments, connected to a non-transitory computer readable medium (not shown) that stores a program for execution by the processor 420. The program includes instructions that cause the processor to process the digitized signal stored in the memory 418 to extract vital signs, gestures, positioning, movement and the like from the digitized signal data. In some embodiments, the processor 420 may use digitized signals from one or more radar sensors 404, or from one or more radar sensors 404 having one or more receivers 408 to, for example, gather macro-doppler data and micro-doppler data separately for processing into different data outputs. The processor 420 may then provide data or alerts to a user on a user interface 428 such as a display, through a speaker, or the like through a communications interface 430. In some embodiments, the processor 420 may also provide data to remote or cloud storage 432 or a mobile device 426 for remote storage, analysis or tracking.

Figure 5:
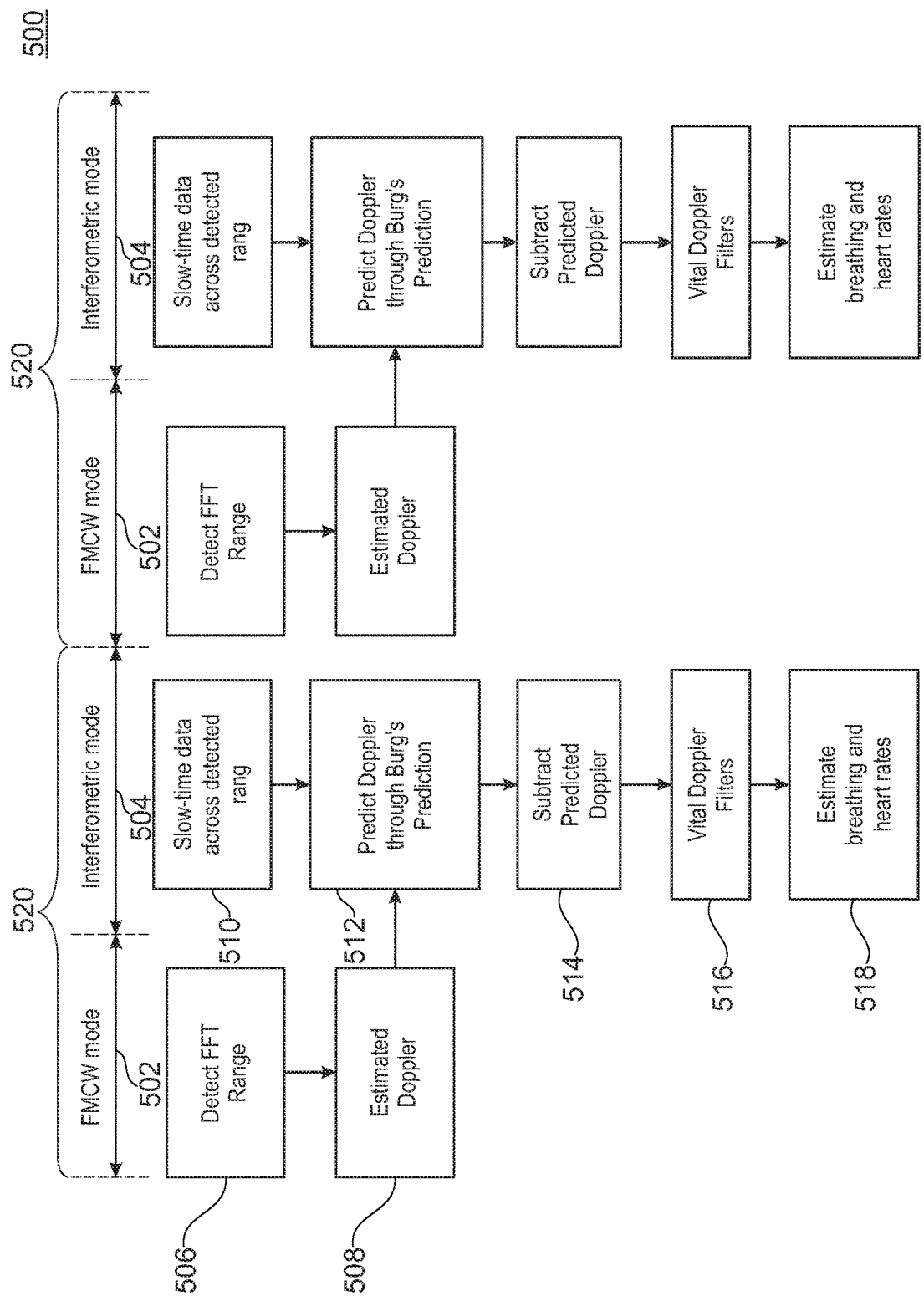
FIG. 5 illustrates a method for vital sensing using predicted doppler according to some embodiments.

FIG. 5 illustrates a method 500 for vital sensing using predicted doppler according to some embodiments. The method 500 may be performed on signals received at the first radar, and may include one or more periods 520, with each period 520 having multiple observation windows 502, 504 in which different radar modes may be used to determine different sensed features. For example, one observation window may be used to detect macro-doppler signals, and another observation window may be used to detect micro-doppler movements. In some embodiments, each period 520 may include a frequency modulated continuous wave (FMCW) window 502 using macro-doppler to detect running motion, gestures, posture, user position, or the like. Each period 520 may also include an interferometric window 504 using vital-doppler to detect vital signs or the like.

In some embodiments, data collected in one observation window 502, 504 may be used in processing a data signal collected in another observation window 502, 504. For example, the doppler generated or calculated in the FMCW window 502 may be used to filter the vital-doppler vital sensing signal in the interferometric window 504.

The FMCW window 502 may include detection of an FFT range in block 506. The FFT range detection may include performing an FFT on a received signal, and range gating the signal to determine a range to large objects in the radar beam, such as a user's torso, arms or head. In some embodiments, the range gating may be used to filter out spurious signals and to isolate gross or macro user movements from other movements, objects or noise. In some embodiments, a two-dimensional FFT may be taken for a range FFT over slow-time to determine the velocity of each detected object. Alternatively, the velocity of each object may be determined by other waveform techniques including, but not limited to triangular chirp and staggered pulse repetition time (PRT).

In block 508, the doppler for the gross user motion is estimated and stored for use in the vital sensing signal processing. The doppler for the gross user motion may then be processed for gesture sensing, user position calculation and adjustment. Thus, the FMCW window 502 may be used to compute the motion of the person. This motion may appear at a single range bin within the period 520 and be represented by the Doppler frequency corresponding to the running motion of the person.

During the interferometric window 504, slow-time data across the detected range is determined in block 510. The slow time data is used to predict the doppler for vital sensing using, for example, a Burg's prediction technique in block 512. The estimated doppler from the FMCW window 502 may also be used in the Burg's prediction technique to account for the gross user motion. In block 514, the predicted doppler generated in block 512 is subtracted or otherwise removed from the radar signal data received during the interferometric window 504. One or more vital doppler filters are applied in block 516 and, in some embodiments, may amplify data at relevant frequencies associated with vital signs, or may be used to attenuate unwanted data, remove noise, or the like. The filtered data is then used to estimate the breathing and heart rates of a user in block 518. For example, the slow time radar signal from the specific/identified target range gate is fed into a band pass filter to determine the breathing rate. For example, a band-pass filter centered around 0.4 Hz with a bandwidth of 0.5 Hz can be used. Alternatively, other center frequencies and bandwidths may be used. Additionally, the filtered data may also be used to recognize an emergency condition that causes the treadmill to perform an emergency stop, control the treadmill operating conditions, such as adjusting the speed or incline of the belt, or respond to a user command, such as changing a display channel. The process of detecting a user's movement and vital signs may then be repeated in subsequent periods 520.

Figure 6:
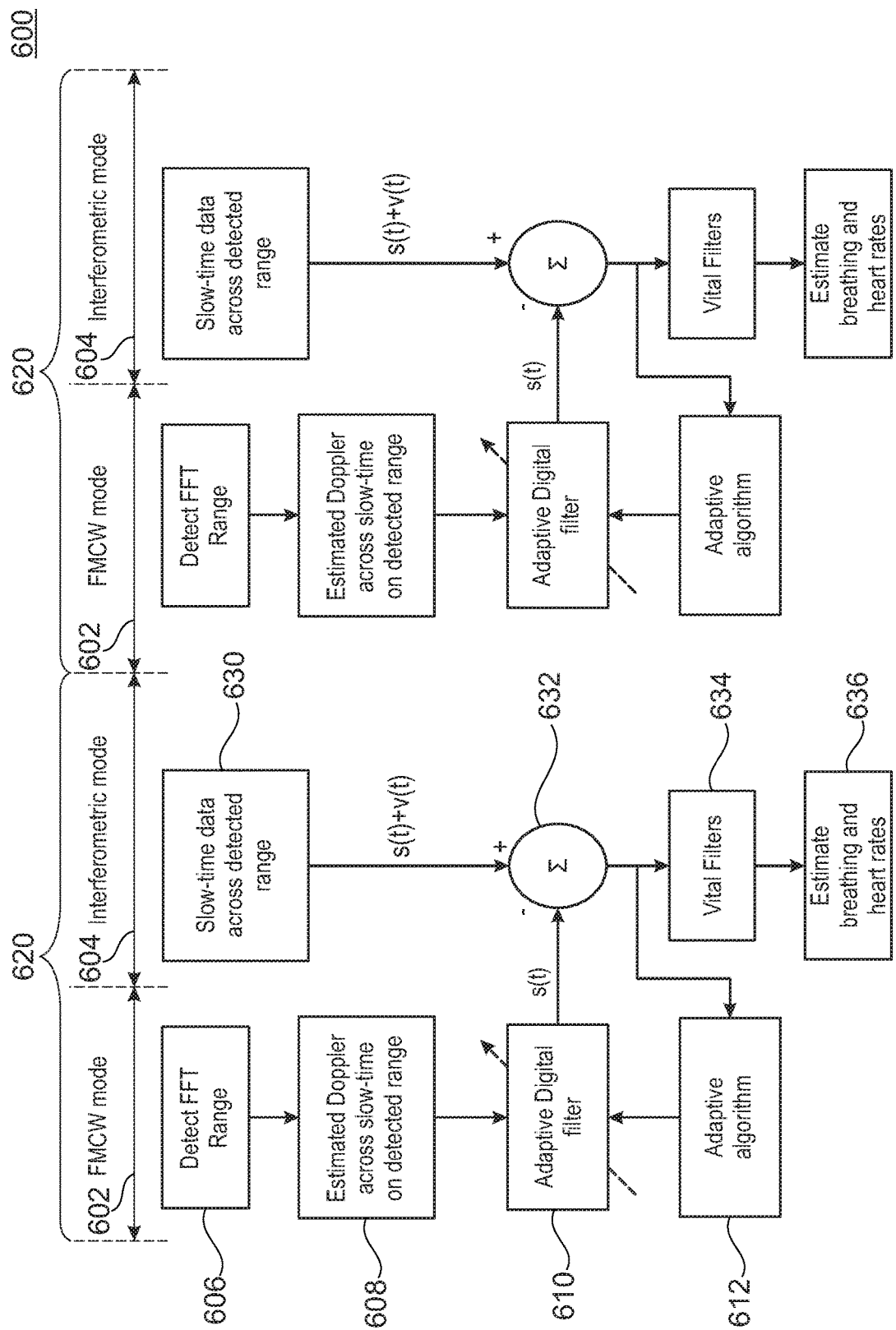
FIG. 6 illustrates a method for vital sensing using an adaptive filter according to some embodiments.

FIG. 6 illustrates a method 600 for vital sensing using an adaptive filter according to some embodiments. The method 600 may be performed using signals received at the first radar in a manner similar to the method 500 of FIG. 5, and with an adaptive filter used to predict doppler for the slow time data signal. The method 600 includes one or more periods 620, with each period 620 having multiple observation windows 502, 504 that, in some embodiments, may include a frequency modulated continuous wave (FMCW) window 602 used to detect gross motion, gestures or running motion, and an interferometric window 604 used to detect vital signs.

In the FMCW window 602, an FFT range is detected in block 606, and in block 608, doppler is estimated across slow-time for the detected range. An adaptive digital filter is applied in block 610 to generate an estimated macro motion signal s(t). The adaptive digital filter may use a persistent adaptive value that is generated by an adaptive algorithm in block 612 based on feedback related to vital signals calculated in a previous observation window.

In the interferometric window 604, slow-time data across the detected range is determined in block 630 to generate a slow time signal s(t)+v(t), which includes vital sign signals v(t) and macro motion signals s(t). In block 632, the estimated macro motion signal s(t) is filtered out of the slow time signal s(t)+v(t). In some embodiments, the filtering is performed using a summer, adder, counter, filter, or the like to subtract or otherwise remove the macro motion signal s(t) from the slow time signal s(t)+v(t) to generate one or more raw vital signals v(t) that may be filtered using a vital filter in block 634, and then used to estimate breathing and heart rates for the user in block 636. The processes in the FMCW window 602 and interferometric window 604 may be repeated one or more times to update the values determined for motion and vital signs. Additionally, the adaptive digital filter may maintain the feedback values across multiple periods 620, with feedback values from one or more periods 620 used to adjust the adaptive digital filter.

Figure 7:
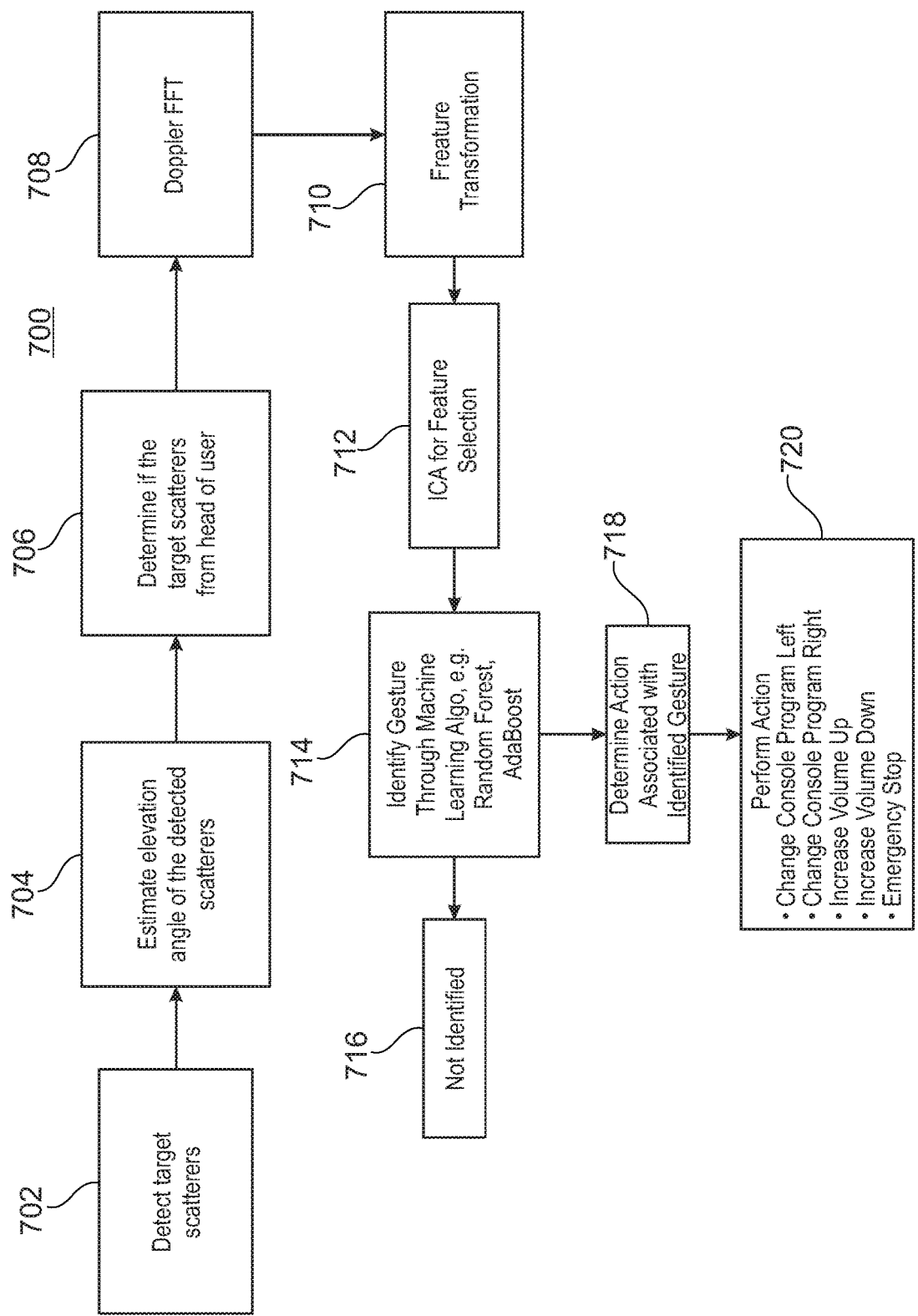
FIG. 7 illustrates a method for gesture sensing in a contactless sensing treadmill according to some embodiments.

FIG. 7 illustrates a method 700 for gesture sensing in a contactless sensing treadmill according to some embodiments. The method 700 may be performed using signals received by the first radar during, for example, the FMCW windows (See FIG. 5, element 502; FIG. 6, element 602). In some embodiments, the treadmill transmits a millimeter-wave radar beam and detects the reflected signal. In block 702 target scatterers are detected. The target scatterers may be detected from the reflected signal, for example, by associating stronger return signals with the target scatterers. In block 704, the elevation angle of the detected scatterers is estimated.

In block 706, the treadmill determines whether the target scatterers are the head of a user. The treadmill may, in some embodiments, analyze data points in the reflected signal and associate large scatterers that have elevations within a predetermined range to be from a user's head, or may determine the target scatterer with the highest elevation to be the user's head, with the assumption that other scatterers with a lower elevation are from the user's torso, arms, or legs. Thus, false readings or commands from arm gestures, shoulder or torso movements while the user is running, or the like, may be avoided. In other embodiments, the treadmill may focus on user arm movements or the like to detect user hand or arm gestures.

In block 708, a Doppler FFT is applied to the reflected signal. Doppler FFT captures the motion signature of the head. In some embodiments, the reflected signal data is filtered to remove noise or amplify the portions of the return signal data identified as being a target scatterer from the user's head. In block 710, the treadmill performs feature transformation on the filtered signal to generate transformed feature data. The feature transformation of block 710 stiches together the Doppler FFTs from multiple FMCW windows of (see, e.g., FIG. 4, element 402) to create a 2D image.

In block 712, the treadmill optionally performs independent component analysis (ICA) on the transformed feature data. In some embodiments, the ICA includes reduction of dimensionality of the transformed feature data to simplify subsequent analysis in a machine learning process. The multiple Doppler images or maps combined in the feature transformation block of 710 may result in a relatively high number of dimensions required for analysis, and may result in sparse data sets with reduced statistical significance (also known as the curse of dimensionality). The ICA of block 712 may be used to reduce the number of dimensions created by multiple Doppler images, improving subsequent gesture recognition.

In block 714, the gesture is identified through, for example, a machine learning algorithm such as a random forest algorithm, adaptive boosting (adaboost) algorithm, XGBoost or another suitable algorithm. The images created by the feature transformation of block 710, or the image data generated by the ICA of block 712 are used for the gesture identification of block 714.

For example, based on the window size, in some embodiments, the FMCW window (FIG. 5, element 502; FIG. 6, element 602) and interferometric window (FIG. 5, element 502; FIG. 6, element 602) could be 1ms. The gesture segment may extend over 2-3 seconds, resulting in thus 1000-1500 Doppler FFT vectors generated in block 708. These Doppler FFT vectors may then be stitched together over time in block 710 to create a 2D image that is used directly in the gesture recognition of block 714, or that is used processed in the ICA of block 712 before the gesture recognition of block 714.

If the gesture is not identified, then, in block 716, the treadmill recognizes that the gesture is not identified and ignores or discards any motion that is detected in the returned signal. If the gesture is identified, then in block 718, the treadmill determines an action associated with the gesture. In block 720, the action associated with the identified gesture is performed. In some embodiments, a database stores gestures and the associated action, and the treadmill may perform the action associated with the determined gesture. In some embodiments, the action may be changing a program such as a video, tracking application or the like that is shown on a display of the treadmill, for example, by switching the active program left or right to the next or previous program. Thus, the treadmill may determine that a user turns their head to the right or left, and change a program played on a display accordingly, for example, by changing a channel or selected program. The treadmill may also determine that a user raises their head up or down and adjust the volume of a program played by the treadmill accordingly. In yet other embodiments, the action may include treadmill executing an emergency stop, stopping the treadmill belt. For example, if the user appears to drop their head, or move their head out of the normal range of positions for a user's head, the treadmill may determine that the user has fallen or injured themselves, and may execute the emergency stop.

Figure 8:
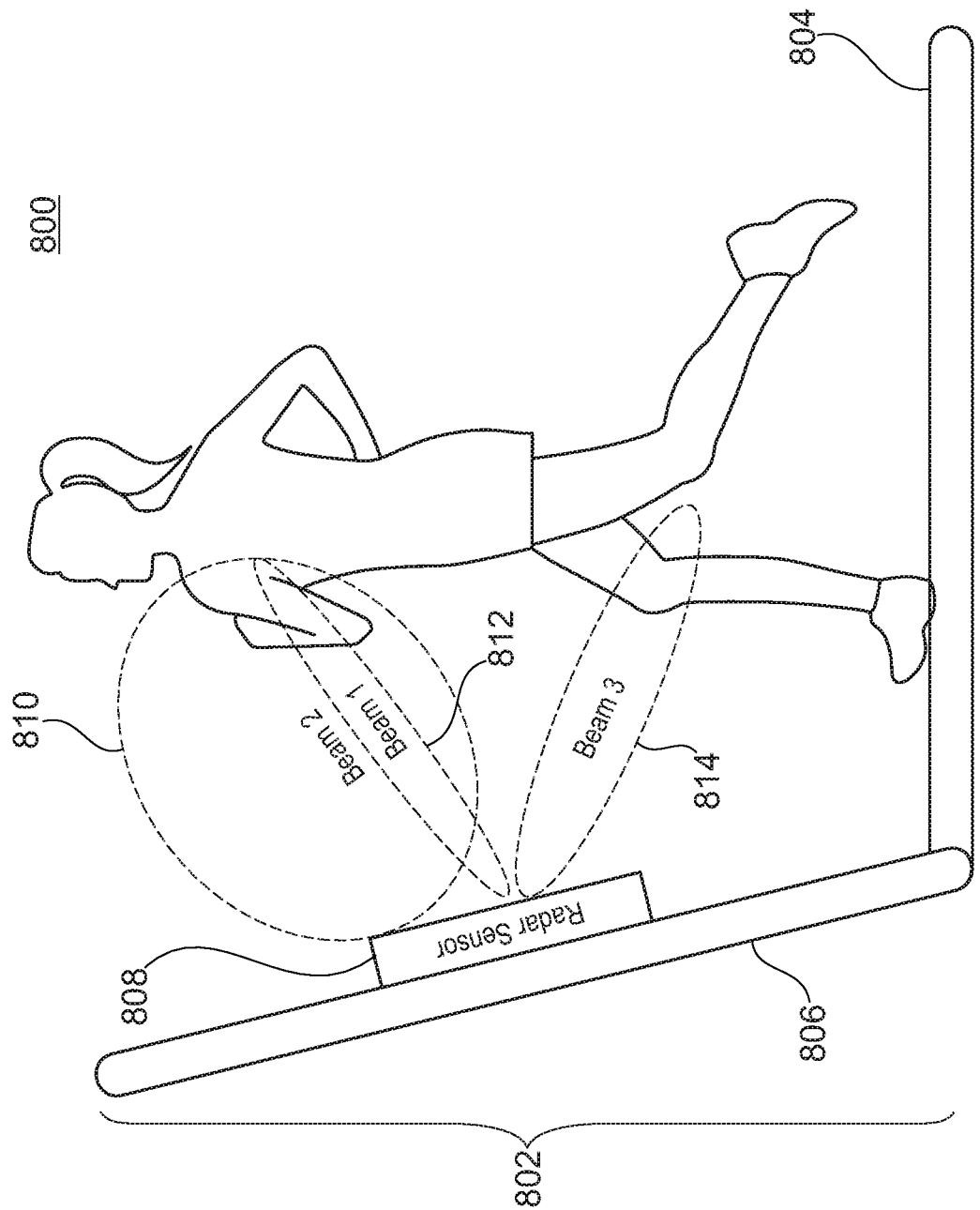
FIG. 8 illustrates a contactless sensing treadmill system according to some embodiments.

FIG. 8 illustrates a contactless sensing treadmill system 800 according to some embodiments. In some embodiments, the system 800 is a treadmill 802 having a belt 804 that moves, permitting a user to run on the treadmill 802. A podium or support 806 supports a radar sensor 808 that may transmit and detect multiple beams 810, 812, 814. In some embodiments, the radar sensor 808 is a single radar sensor with multiple transmitter (TX)-receiver (RX) system with multi-beam capabilities that perform multiple operations using specified modulation parameters. The reflections of the beams 810, 812, 814 may be used with the modulation parameters to channelize the received signals and avoid interference between the multiple beams 810, 812, 814.

A first beam 812 may be a narrow beam that gathers data for vital sensing, and may be focused on a user's torso region. The data gathered through the first beam 812 may be used to detect a user's vital signs. A second beam 810 may be a wider beam that gathers data for gesture sensing and control, and data gathered from the second beam 810 may be used to automatically operate or control the treadmill 802, allow the user to adjust machine parameters manually, or the like. A third beam 814 may be directed at another portion of the user, such as the user's legs. The third beam 814 detects major movement and the data gathered by the third beam may be used to develop a Doppler map to extract the speed or position of the user, and precisely determine distance covered, calories burned, or the like.

FIGS. 9A through 9C illustrate various scenarios for control of a treadmill 902 based on user 914 positioning according to some embodiments. A radar sensor 904 continuously measures the distance to the torso of a user 914 walking or running on the moving belt 908 of the treadmill. When the user 914 approaches too closely to the front of the treadmill 902, the treadmill speed and/or the treadmill slope are increased, and when the person user 914 moves too far away from the front of the treadmill 902, the treadmill speed and/or the treadmill slope are decreased. In some embodiments, the response of the treadmill speed and/or slope control system is a non-linear response system. Thus, when the user 914 is closer to the front of the treadmill 902, the rate of increase of the treadmill speed and/or slope is higher compared to when the user 914 is closer from its earlier running position. Therefore, the nonlinear response system adjusts the speed of the treadmill 902, the slope of the treadmill belt, or both the speed and slope of the treadmill belt according to the deviation of the user's actual position from a selected user position or position range. The radar sensor 904 also determines the maximum user safe region or limit 912 and checks whether the user 914 crosses outside of the user safe region or limit 912, and may immediately shuts down the treadmill belt 908. The radar sensor 904 may also determine the distance covered by the user through the Doppler frequency and the range migration experienced through the exercise.

FIG. 9A illustrates a scenario 900 where a user 914 is within a user safe limit 912. When the user 914 runs or walks on a belt 908 of a treadmill 902, a radar sensor 904 uses a millimeter-wave beam 906 to detect a distance to a user 914. When the user 914 is within the user safe limits 912, the radar sensor 904 detects the user 914 at a first distance 910 and that the user 914 is between a first threshold 916 and a second threshold 918. When the user 914 is between the first threshold 916 and second threshold 918, the treadmill 902 may determine the user is within the user safe limits 912. The treadmill 902 may maintain the speed, incline of the belt, or adjust a belt control program for the user 914 while the user 914 remains within the user safe limits 912.

FIG. 9B illustrates a scenario 920 where a user 914 approaches the front of a user safe limit 912. When the radar sensor 904 detects that the user 914 is at a second distance 922, the treadmill 902 may determine that the user 914 has moved outside of the user safe limits 912, or approached a first threshold 916 that may be a boundary of a user safe limit 912. Therefore, the treadmill 902 determines, according to the second distance 922, that the user 914 has passed first threshold 916. The treadmill 902 may then adjust the speed or incline of the belt 908, or adjust a belt control program to cause the user 914 to move backward along the belt 908. For example, when the user 914 approaches the front of the belt 908, near the first threshold 916, the treadmill 902 may raise the incline, or increase the speed of the belt 908 so that the user 914 moves backward toward the center of the belt 908 to stay within the user safe limits 912.

FIG. 9C illustrates a scenario 940 where a user 914 approaches the rear of a user safe limit 912. When the radar sensor 904 detects that the user 914 is at a third distance 942, the treadmill 902 may determine that the user 914 has moved outside of the user safe limits 912, or approached a second threshold that may be boundary of a user safe limit 912. Therefore, the treadmill 902 determines, according to the third distance 942, that the user 914 has passed second threshold 918. The treadmill 902 may then adjust the speed or incline of the belt 908, adjust a belt control program to cause the user 914 to move rearward along the belt 908, or execute an emergency stop. For example, when the user approaches the rear of the belt 908, near the second threshold 918, the treadmill 902 may lower the incline, or decrease the speed of the belt 908 so that the user 914 moves backward to the center of the belt 908 to stay within the user safe limits 912. The treadmill 902 may also determine that the user has moved too near the rear of the belt 908 and may execute an emergency stop to prevent the user from falling off the treadmill 902.

Figure 10:
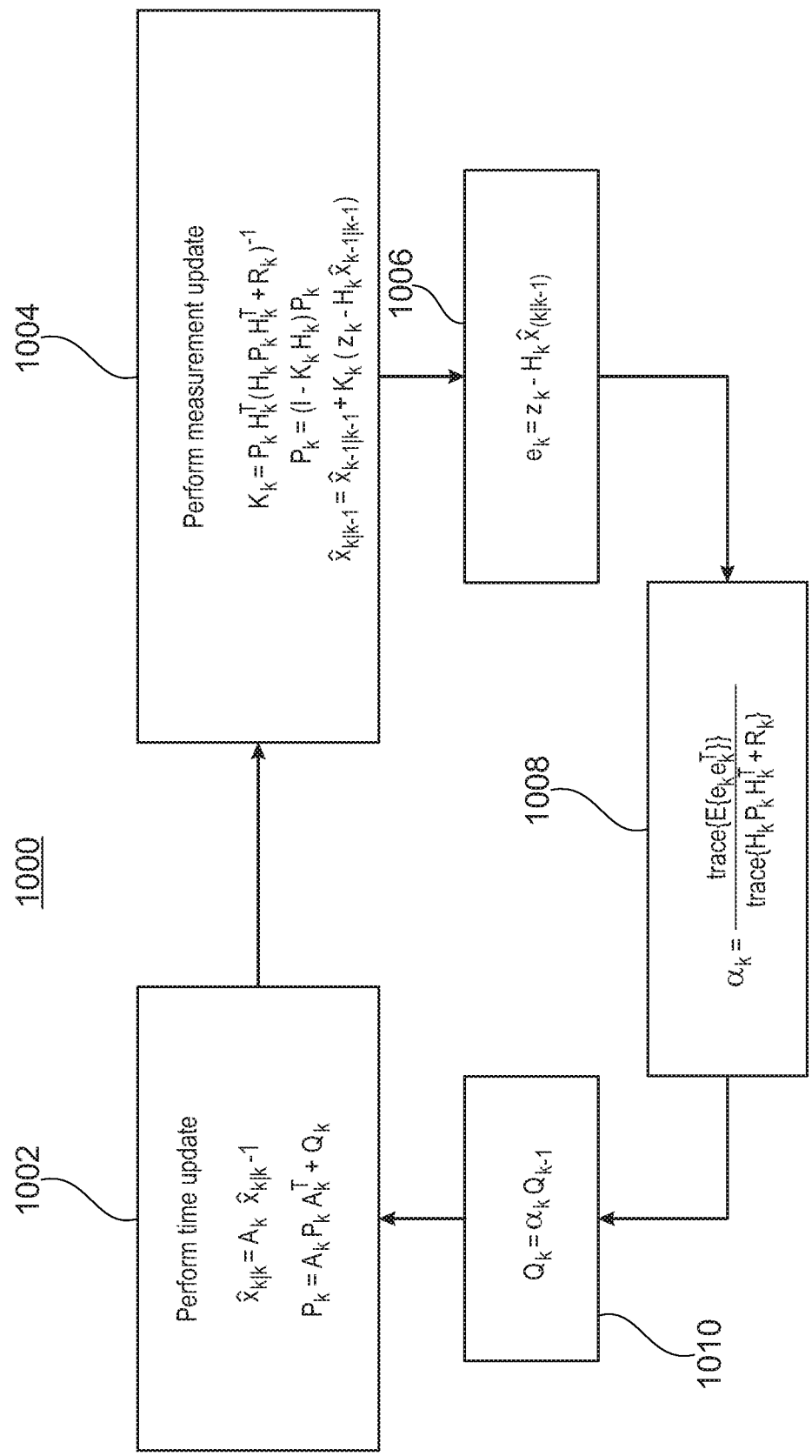
FIG. 10 illustrates a method for user position and velocity tracking in a contactless sensing treadmill according to some embodiments.

FIG. 10 illustrates a method 1000 for user position and velocity tracking in a contactless sensing treadmill according to some embodiments. A statistical prediction algorithm to estimate or predict a user's position on the treadmill belt. In some embodiments, the algorithm is a linear quadratic estimate (LQE) such as a Kalman filter, a state estimator, or another dynamic feedback system. Embodiments using a Kalman filter may, for example, use a standard Kalman filter, a frequency weighted Kalman filter, an extended Kalman filter, a Kalman-Bucy filter, a hybrid Kalman filter, or the like.

In some embodiments, the extended Kalman filter is used to project a state of the user's position and an error associated with the projection. The Kalman filter then adjusts the position and error according to feedback resulting from measurements of the user position. The Kalman filter may use variable matrices for a constant velocity model, which may include:

$$\hat{x_k} = [r_k, v_k] \qquad (1)$$

$$H_k = \begin{bmatrix} 1 & 0 \\ 0 & 1 \end{bmatrix} \qquad (2)$$

$$A_k = \begin{bmatrix} 1 & \delta t \\ 0 & 1 \end{bmatrix} \qquad (3)$$

$$R_k = \begin{bmatrix} r_{err}^2 & 0 \\ 0 & v_{err}^2 \end{bmatrix} \qquad (4)$$

In the method 1000 for user position and velocity tracking, a time update is performed in block 1002. A position $\hat{x}_{k|k}$ at step or time k may be estimated according to:

$$\hat{x}_{k|k} = A_k \hat{x}_{k|k-1} \qquad (5)$$

where $\hat{x}_{k|k}$ is the a posteriori estimate of the user position at step or time k, $A_k$ is a process Jacobian variable at time k, and $\hat{x}_{k|k-1}$ is the apriori, or previous, estimate of the user position at step or time k-1. The estimated error covariance associated with $\hat{x}_{k|k}$ may be estimated according to:

$$P_k = A_k P_k A_k^T + Q_k \qquad (6)$$

where $P_k$ is the a priori estimate of the error covariance at time k, $A_k^T$ is the transpose of $A_k$, and $Q_k$ is the process noise covariance at time k and may be a matrix in which an unknown acceleration is factored.

In block 1004, a measurement update is performed to calculate the Kalman gain $K_k$ and update the estimated values $\hat{x}_{k|k}$ and $P_k$. The Kalman gain may be determined according to:

$$K_k = P_k H_k^T (H_k P_k H_k^T + R_k)^{-1} \qquad (7)$$

where $K_k$ is the Kalman gain, $H_k$ is a process Jacobian variable at time k, $H_k^T$ is the transpose of $H_k$, and $R_k$ is the measurement error covariance at time k. The estimated error covariance $P_k$ may be updated according to:

$$P_k = (I - K_k H_k) P_k \qquad (8)$$

where I is the identity matrix. The estimated user position $\hat{x}_{k|k}$ may be updated and set to $\hat{x}_{k|k-1}$ according to:

$$\hat{x}_{k|k-1} = \hat{x}_{k-1|k-1} + K_k(z_k - H_k \hat{x}_{k-1|k-1}) \qquad (9)$$

where $\hat{x}_{k-1|k-1}$ is the estimated user position for time k-1 at time k-1, and $z_k$ is the actual measurement vector.

In block 1006, the innovation, or measurement prefit residual is calculated. An a posteriori estimate error measurement $e_k$ is determined according the actual measurement vector $z_k$, and may be determined according to:

$$e_k = z_k - H_k \hat{x}_{(k|k-1)} \qquad (10)$$

In block 1008, an adaptation factor $\alpha_k$ is determined according to:

$$\alpha_k = \frac{\text{trace}\{E\{e_k e_k^T\}\}}{\text{trace}\{H_k P_k H_k^T + R_k\}} \qquad (11)$$

where E is the a posteriori error covariance matrix, $e_k$ is the a posteriori error at step k, and $e_k^T$ is the transpose of $e_k$.

In block 1010, the process noise covariance $Q_k$ is dynamically adjusted according to the adaption factor $\alpha_k$, and is determined according to:

$$Q_k = \alpha_k Q_{k-1} \qquad (12)$$

where $Q_k$ is the process noise covariance at time k, and $Q_{k-1}$ is the proces noise covariance at time k-1. The process noise covariance $Q_k$ may then be used in the time update of block 1002 for a next time segment.

Figure 11:
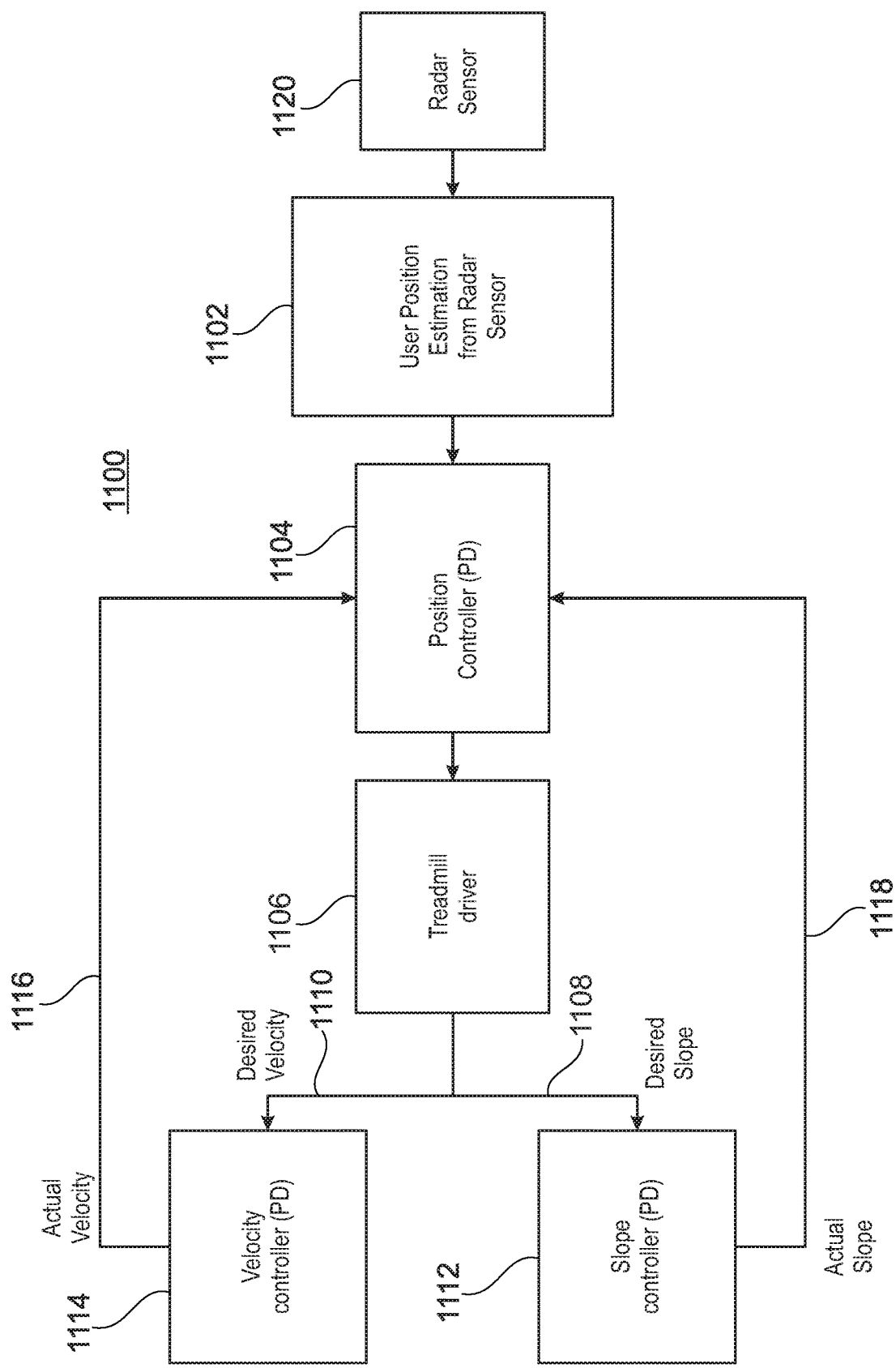
FIG. 11 illustrates a system for controlling a treadmill according to some embodiments.

FIG. 11 illustrates a system 1100 for controlling a treadmill according to some embodiments. The system 1100 may be disposed in a treadmill, and may include a position controller 1104 that received a user position estimation signal 1102 from one or more sensor modules 1120, from a processor that is connected to one or more sensor modules 1120, or the like. The position controller 1104 may determine a desired position for a user according to the user position estimate, and may receive an actual velocity signal 1116 as feedback from a velocity controller 1114 and actual slope signal 1118 as feedback from a slope controller 1112. In some embodiments, the position controller 1104 is a proportional-derivative controller (PD), and may be implemented as a processor connected to a non-transitory computer readable medium that stores program instructions that cause the processor to determine a desired user position and generate a position control signal for controlling a treadmill driver 1106.

The treadmill driver 1106 may, in some embodiments, be a control circuit that receives the position control signal from the position controller 1104. The treadmill driver 1106 generates a desired velocity signal 1110 and a desired slope signal 1108 according to the positon control signal. The treadmill driver 1106 provides the desired velocity signal 1110 to a velocity controller 1114 and provides the desired slope signal 1108 to the slope controller 1112.

The velocity controller 114 and slope controller 1112 may each be a PD, and may control a motor, motor controller, or the like, that drives the treadmill belt at a desired speed, or changes the incline of the treadmill belt to achieve the desired slope. For example, the velocity controller 1114 may receive the desired velocity signal 1110 from the treadmill driver 1106 and control a treadmill belt drive motor to achieve the desired velocity indicated by data in the desired velocity signal 1110. In some embodiments, the velocity controller 1114 determines the actual speed of the treadmill belt, for example, through a sensor reading the revolutions per minute (RPM) of the treadmill belt drive motor, by determining the RPM or a speed associated with a control signal provided to the treadmill belt drive motor, by a current draw of the treadmill drive motor, or the like. The velocity controller 1114 adjusts the actual speed of the treadmill belt according to the desired speed. In embodiments where the velocity controller 1114 is a PD controller, the velocity controller 1114 uses a proportional-derivative feedback system to determine the adjustment needed to change the actual treadmill velocity to match the desired velocity indicated by the desired velocity signal 1110. Additionally, the velocity controller 1114 may provide an actual velocity signal 1116 to the position controller 1104, with the actual velocity signal 1116 determined according to, for example, the RPM of a treadmill belt drive motor, a speed of the treadmill belt measured by a feedback sensor, the determined actual speed of the treadmill belt, or the like.

Similarly, the slope controller 1112 may receive the desired slope signal 1108 from the treadmill driver 1106 and control a treadmill belt slope driver, controller, system or motor to achieve the desired slope indicated by data in the desired slope signal 1108. In some embodiments, the slope controller 1112 determines the actual slope or incline of the treadmill belt, for example, through a sensor reading a height of a drive motor or height measurement element, a height associated with a control signal provided to the treadmill belt elevation or slope motor, or the like. The slope controller 1112 adjusts the actual slope of the treadmill belt according to the desired slope. In some embodiments, where the slope controller 1112 is a PD controller, and uses a proportional-derivative feedback system to determine the adjustment needed to change the actual treadmill slope to match the desired slope indicated by the desired slope signal 1108. Additionally, the slope controller 1112 may provide an actual slope signal 1118 to the position controller 1104, with the actual slope signal 1118 determined according to, for example, the extension of a belt slope adjustment mechanism or the treadmill belt slope determined by a feedback sensor.

Figure 12:
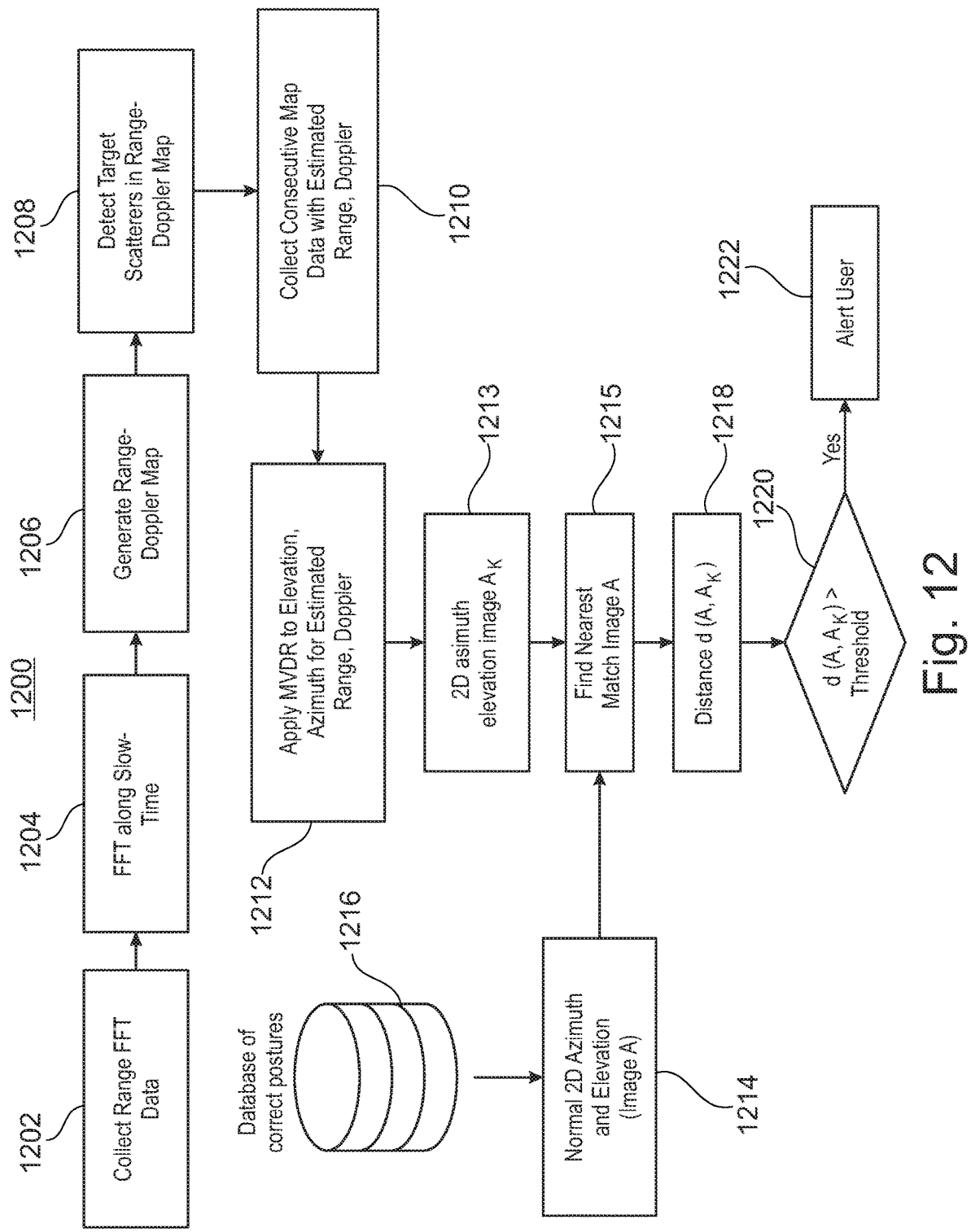
FIG. 12 illustrates a method for posture analysis on a treadmill according to some embodiments.

FIG. 12 illustrates a method for posture analysis on a treadmill 1200 according to some embodiments. In block 1202, the treadmill collects range FFT data from a received signal. The received signal may be a signal reflected from a user's torso, and range gate or range FFT data may be calculated on the received signal. In block 1204, an FFT is performed along slow time according to the range FFT data.

In block 1206, one or more range-doppler maps are generated as a result of the FFT along slow time. The FFT across slow time creates a 2D range-doppler image for a particular observation window. In block 1208, target scatters or targets may be detected from the 2D range-doppler map. In some embodiments, the target's range and doppler may be estimated using the 2D range-doppler map. Values in the 2D range-doppler map may be compared to a threshold, with large signals that exceed the threshold being identified as a target within the map. The range and Doppler for the identified targets may then be estimated. In block 1210, a series or range-doppler maps may be generated, by performing block 1202 through 1208 multiple times, or multiple range-doppler maps may be generated from a single received signal. Data may be collected from all virtual antennas in a sensor across multiple FMCW windows, and data that has the about the same range and doppler may be stacked as a vector. For example, the combined data C may be determined as a matrix and the matrix $C[E(x(\ )x(\ )^H)]$ may be computed as:

$$\frac{1}{N}\sum_{n=1}^{N} x(\text{range, doppler})^n x(\text{range, doppler})^{nH} \quad (13)$$

where x( ) is a vector with data received across all antennas (N_TX, N_RX), N is the number of FMCW windows from which the range and Doppler information is taken, and in some embodiments, is greater than the number of transmitters (N_TX) multiplied by the number of receivers (N_RX) to avoid low ranked matrices.

In block 1212, a minimum variance distortionless response (MVDR) algorithm is applied to the range and doppler data. For example, the time delay $\tau_{ij}$ of a radar return from a scatterer ij at a base distance x from the center of the virtual linear array at azimuth angle θ and elevation angle φ may be determined according to:

$$\tau_{ij} = \frac{2x}{c} + \frac{2d_{ij}\sin(\theta)\cos(\varphi)}{c} \quad (13)$$

where $d_{ij}$ is the 3D position of the virtual element to the center of the virtual array.

The transmit steering vector $\alpha_i^{Tx}$ for transmitter i is determined according to:

$$a_i^{Tx}(\theta, \varphi) = \exp\left(-j2\pi \frac{d_i^{Tx}\sin(\theta)\cos(\varphi)}{\lambda}\right); i = 1, 2 \quad (14)$$

where λ is the wavelength of the transmit signal and $d_i^{Tx}$ is the 3D positional coordinate of transmitter element i. The receiving steering vector $\alpha_j^{Rx}$ or transmitter j is determined according to:

$$a_j^{Rx}(\theta, \varphi) = \exp\left(-j2\pi \frac{d_j^{Rx}\sin(\theta)\cos(\varphi)}{\lambda}\right); j = 1, 2 \quad (15)$$

where $d_i^{Tx}$ is the 3D positional coordinate of transmitter element i. The azimuth and elevation imaging profile P(θ, φ) for a given range x is determined according to $$P(\theta, \varphi) = \frac{(a^{Tx}(\theta, \varphi) \otimes a^{Rx}(\theta, \varphi))^H (a^{Tx}(\theta, \varphi) \otimes a^{Rx}(\theta, \varphi))}{(a^{Tx}(\theta, \varphi) \otimes a^{Rx}(\theta, \varphi))^H C (a^{Tx}(\theta, \varphi) \otimes a^{Rx}(\theta, \varphi))}; \quad (16)$$

where C( ) is the combined data C from Equation 13, and ⊗ is the Kronecker product of two vectors. Thus, the Kronecker product $\alpha^{Tx}(\theta, \varphi) \otimes \alpha^{Rx}(\theta, \varphi)$ of the steering vector of the transmitter array $\alpha^{Tx}(\theta, \varphi)$ and the steering vector of the receiver array $\alpha^{Rx}(\theta, \varphi)$ may be determined, and be used to resolve the relative azimuth and elevation angles of the scatterer θ, φ using equation 16.

In block 1213, an azimuth elevation image $A_k$ is generated according to the azimuth and elevation imaging profile P(θ, φ). In some embodiments, the azimuth and elevation imaging profile may be used as the azimuth elevation image, and in other embodiments, the azimuth elevation image is selected according to the azimuth and elevation imaging profile, is generated from further processing of the azimuth and elevation imaging profile, or the like.

The treadmill then attempts to match the user's posture to a posture stored in a posture database 1216. In block 1214, the treadmill accesses the database of correct postures 1216, and in block 1215 nearest posture (A) is selected as a potential match. For example, the posture database 1216 are saved 2D elevation, azimuth images of correct/good postures, and may include maps of user standing, walking, jogging, and running. The treadmill may use the series of range-doppler maps to determine the user's current action by matching the range-doppler maps or detected posture to the nearest stored posture data. In some embodiments, the elevation and azimuth image $A_k$ is the input to a posture estimation unit, which compares the elevation and azimuth image $A_k$ to the postures in the database of correct postures 1216. In some embodiemtns, a simple instance-based machine learning algorithm, such as nearest neighbor (NN) algorithm is used in this case, comparing the estimated 2D elevation and azimuth image $A_k$ to saved 2D images to determine the nearest saved image A from the database of correct postures that is closest to the estimated 2D elevation and azimuth image $A_k$.

In block 1218, the treadmill determines the distance d(A, $A_k$) between the user posture $A_k$ and the nearest posture A to determine whether the user's posture is correct. In some embodiments, determining the distance $d(A, A_k)$ may include determining the difference between various points of the user posture $A_k$ and the nearest posture A. The treadmill, in block 1220, then determines whether the distance $d(A, A_k)$ is greater than a predetermined threshold, and if so, the treadmill determines that the user's posture is not correct. For example, the distance $d(A, A_k)$ may be a sum, average, deviation, or the like of the differences between one or more points of the user posture $A_k$ and the nearest posture A, then the treadmill may determine that the user's posture is not correct, or out of line, and may, in block 1222, alert the user. For example, if a user is running with a longer stride with one leg, if the user's torso is slumped, or the user's posture has another irregularity, the treadmill may provide an alert to the user to adjust their posture, and may in some embodiments, illustrate the correct posture based on the nearest posture A.

FIGS. 13A through 13C illustrate radar sensor arrangements according to some embodiments. FIG. 13A illustrates a minimum radar system transceiver configuration 1300 according to some embodiments. In some embodiments, the minimum radar system transceiver configuration 1300 may be a single radar sensor 1302 having a single transmitter 1304 and a single receiver 1306.

FIG. 13B illustrates a linear array radar system transceiver configuration 1320 according to some embodiments. Multiple radar sensors 1324A . . . 1324D may be provided, with each radar sensor 1324A . . . 1324D having at least one transmitter 1328 and receiver 1326.

A sensor module having minimum radar system transceiver configuration 1300 may be used for single beam sensing. For example, a treadmill arrangement where the sensor module performs a single measurement may use a single transmitter 1304 and single receiver 1306 to measure a user's leg movements or position (See, for example, element 312, FIG. 3).

Taking measurements of multiple features may be efficiently implemented in a single sensor module using at least a single transmitter and two or more receivers. For example, a system for measuring gesture and vital signs may be implemented in a single sensor module, with the transmitter transmitting different beams and the two or more receivers used to remove clutter in the detected signals. In some embodiments, the linear array radar system transceiver configuration 1320 may be used for multiple beam sensing, for example, in a treadmill arrangement where the sensor module performs different measurements of user head gestures and vital signs using separate beams for measurement of the different features (See, for example, element 308, FIG. 3). In other embodiments, a single radar sensor with at least one integrated transmitter and two or more integrated receivers may be provided in place of a linear array of sensors.

FIG. 13C illustrates a multi-receiver multi-transmitter radar system transceiver configuration 1340 according to some embodiments. The multi-receiver multi-transmitter radar system transceiver configuration 1340 may be implemented in a single sensor 1342, which takes measurements of user features in different regions (See, for example, element 808, FIG. 8). A single sensor 1342 has multiple transmitters 1346 and multiple receivers 1344. The sensor 1342 may be configured to perform beam scanning with the transmitters 1346 to remove clutter from signals received at the receivers 1344. In some embodiments, the transmitters 1346 may steer beams to different regions, such as the user's torso, head or legs to take measurements of different statistics.

Figure 14:
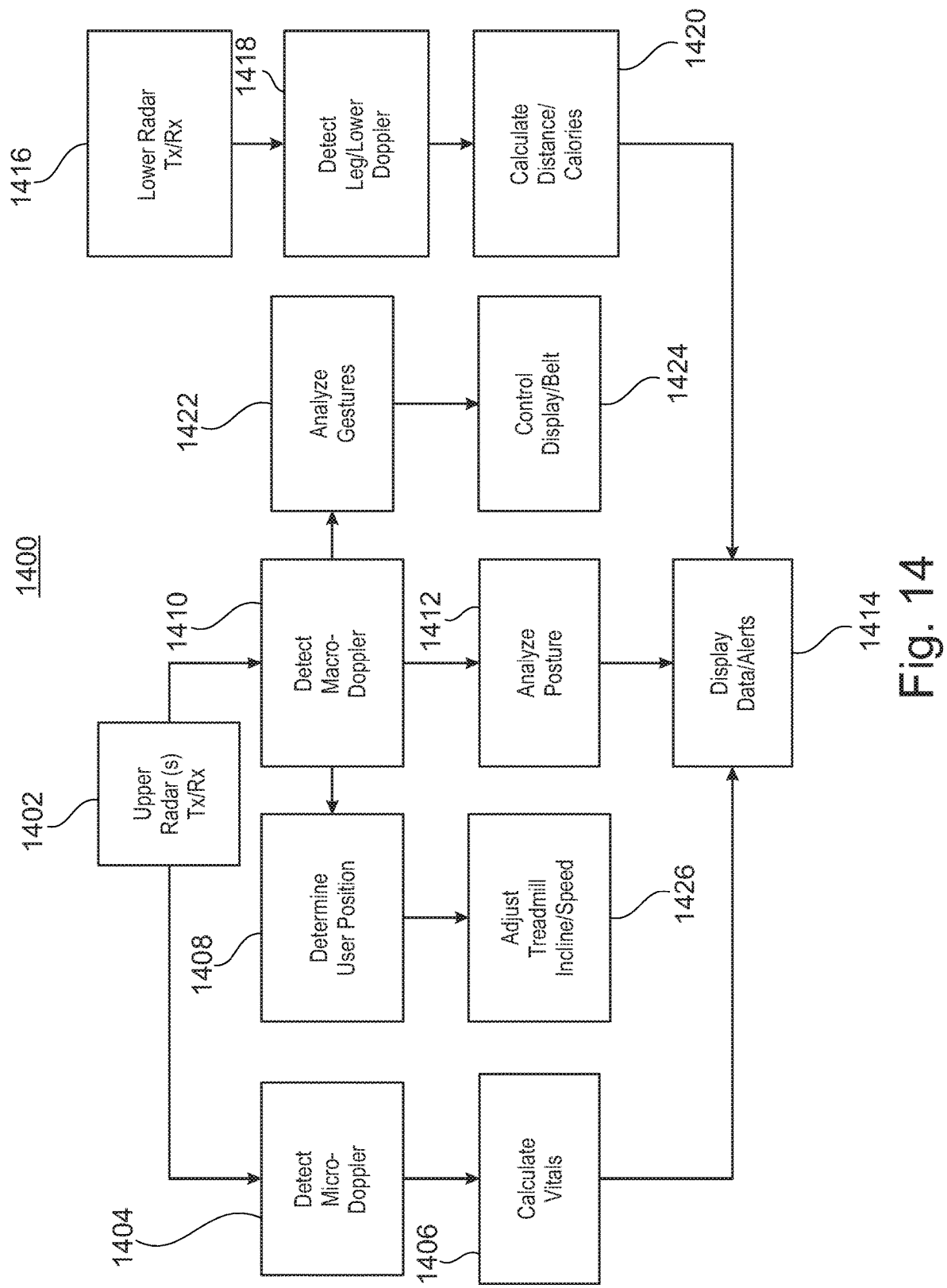
FIG. 14 illustrates a method for operating a treadmill using contactless sensing according to some embodiments.

FIG. 14 illustrates a method 1400 for operating a treadmill using contactless sensing according to some embodiments. In block 1402, an upper radar, or first radar, may transmit millimeter wave radar signals and receive reflected signals. In some embodiments, the upper radar, or first radar may alternate between an FMCW mode and an interferometric mode, and in some embodiments, different radar sensors may transmit multiple beams in turn or simultaneously. A first beam may be used to detect vital signals, and the treadmill, in block 1404 may generate or determine micro-doppler signals. The micro-doppler signals may be reflection signals from a narrow beam or a beam transmitted during an interferometric mode window processed as discussed above. In block 1406, a user's vital signals, such as heart rate or respiration rate may be calculated from the micro-doppler data. In block 1414, the treadmill may display data or an alert reflecting the calculated vital signals to the user. In block 1426, the treadmill may adjust the speed and/or incline of the treadmill belt according to the vital signals. For example, when a user has a heart rate or respiration rate that exceeds a predetermined threshold, the treadmill may lower the speed and/or incline of the treadmill belt to reduce stress on the user. In some embodiments, the speed and/or incline of the treadmill belt may be adjusted proportionally to the user's vital signals, or may shut down completely if the treadmill determines the user is experiencing distress.

The treadmill may also use the macro-doppler data from the upper radar, or first radar, to analyze gestures in block 1422. The treadmill may determine whether a movement of the user's head, arms, or the like, matches a stored gesture map, or the like, and if a match is found, the treadmill may determine that the user has made a predetermined gesture, and in block 1421, may take action based on the identified gesture. For example, the treadmill may, in response to an identified gesture, change a displayed program, adjust a playback volume, execute an emergency stop of the treadmill belt, or perform another control action.

In block 1416, a lower radar, or second radar, may transmit millimeter wave radar signals and receive reflected signals. A beam from the second radar may be transmitted towards a lower portion of the user's body, such as the user's legs, and in block 1418, the treadmill may detect leg doppler signals or doppler signals from the lower radar as a result of the second beam reflecting off the user. In block 1420, the treadmill may calculate the distance travelled by the user, and the calories burned by the user, and, in block 1414, display this data to the user.

Thus, an embodiment treadmill includes a belt, a display, a first sensor having first transmission circuitry for transmitting a first radar beam over the belt and first reception circuitry for detecting a first reflected signal that is a reflection of the first radar beam from a user on the belt, a processor connected to the first sensor, the belt and the display, and a non-transitory computer-readable storage medium storing a program to be executed by the processor. The program includes instructions for determining, according to the first reflected signal, first data associated with a vital sign of the user and displaying, according to the first data, the vital sign on the display.

In some embodiments, the program further includes instructions for detecting, according to the first reflected signal, a gesture of the user while the user is on the belt, and controlling at least one of the belt and the display according to the gesture. In some embodiments, the first transmission circuitry is further configured to transmit a first portion of the first radar beam in a frequency modulated continuous wave (FMCW) mode during a first observation window, and transmit a second portion of the first radar beam in an interferometric mode during a second observation window different from the first observation window. The program further includes instructions for generating estimated range and macro-doppler data from the first portion of the first radar beam, and generating vital-doppler data from the second portion of the first radar beam where the instructions for determining first data associated with the vital sign of the user includes instructions for determining the first data associated with the vital sign of the user according to the vital-doppler data. In some embodiments, the program further includes instructions for determining a user positon according to the estimated range and macro-doppler data, and adjusting an operating parameter of the belt according to the user position. In some embodiments, the instructions for determining the user positon include instructions for determining a measured user position according to the estimated range and macro-doppler data, and the instructions for adjusting the operating parameter of the belt include instructions for adjusting at least one of a speed or an incline of the belt according to a predicted user position determined using a Kalman filter and according to the measured user position. In some embodiments, the program further includes instructions for determining a user gesture according to the macro-doppler data, and controlling the display according to the user gesture. In some embodiments, the instructions for generating the macro-doppler data from the first portion of the first radar beam include instructions for generating estimated doppler data according to the macro-doppler data, and the instructions for determining first data associated with the vital sign of the user includes instructions for determining the first data associated with the vital sign of the user according to the vital-doppler data and the estimated doppler data. In some embodiments, the device further includes a second sensor having second transmission circuitry for transmitting a second radar beam over the belt and second receiving circuitry for detecting a second reflected signal that is a reflection of the second radar beam from legs of the user on the belt, and the program further includes instructions for determining, according to the second reflected signal, leg doppler data, determining a travelled distance for the user according to the first reflected signal, determining a calorie burned amount according to the traveled distance for the user, and displaying the travelled distance and the calorie burned amount on the display.

An embodiment method includes receiving, by a first sensor of a treadmill, a first reflected signal that is a first reflection of a first radar beam reflected from a user on a belt of the treadmill, receiving, by a second sensor of a treadmill, a second reflected signal that is a second reflection of a second radar beam reflected from the user, generating, according to the first reflected signal, first data associated at least one of a gesture of the user or a position of the user on the belt, generating, according to the second reflected signal, second data associated with a vital sign of the user, controlling at least one of the belt and a display of the treadmill according to the first data and displaying, according to the second data, the vital sign on the display.

In some embodiments, the first radar beam is a first portion of a radar transmission in a frequency modulated continuous wave (FMCW) mode during a first observation window, and the second radar beam is a second portion of the radar transmission in an interferometric mode during a second observation window different from the first observation window, and wherein the method further includes generating the first data as macro-doppler data according to the first reflected signal, and generating the second data as vital-doppler data according to the second reflected signal. In some embodiments, the method further includes determining a measured user position according to the macro-doppler data, determining a predicted user position using a Kalman filter and according to the measured user position, and adjusting at least one of a speed or an incline of the belt according to a predicted user position determined using a Kalman filter applied to the measured user position. In some embodiments, generating the macro-doppler data includes generating estimated doppler data according to the macro-doppler data, and generating the second data associated with the vital sign of the user comprises generating the second data associated with the vital sign of the user according to the vital-doppler data and the estimated doppler data. In some embodiments, the method further includes receiving a second reflected signal that is a third reflection of a radar beam from legs of the user on the belt, determining, according to the second reflected signal, leg doppler data, determining a travelled distance for the user according to the first reflected signal, determining a calorie burned amount according to the traveled distance for the user, and displaying the travelled distance and the calorie burned amount on the display.

An embodiment method includes moving a belt of a treadmill, transmitting a first radar beam over the belt toward a user on the belt while the belt is moving, detecting a first reflected signal that is a first reflection of the first radar beam from the user, generating, according to the first reflected signal, first data associated with a vital sign of the user, and displaying, according to the first data, the vital sign on a display of the treadmill.

In some embodiments, the method further includes transmitting a second radar beam over the belt toward the user while the belt is moving, detecting a second reflected signal that is a second reflection of the second radar beam from the user, generating, according to the second reflected signal, second data associated with a gesture of the user, detecting, according to the second data, the gesture, and controlling the display according to the gesture. In some embodiments, transmitting the second radar beam comprises transmitting the second radar beam using a frequency modulated continuous wave (FMCW) mode in an FMCW observation window of a radar transmission, and the transmitting the first radar beam comprises transmitting the first radar beam using an interferometric mode in an interferometric observation window of the radar transmission, where the interferometric observation window is different from the FMCW observation window. In some embodiments, the method further includes determining a measured user position according to the second reflected signal, determining a predicted user position using a Kalman filter and according to the measured user position, and adjusting at least one of a speed or an incline of the belt according to a predicted user position determined using a Kalman filter and according to the measured user position. In some embodiments, the method further includes determining a an estimated azimuth and elevation image according to the second reflected signal and indicative of a posture of the user, determining a nearest correct posture image for the estimated azimuth and elevation image from a set of saved two dimensional (2D) elevation and azimuth images of correct postures, determining a difference between the estimated azimuth and elevation image and the nearest correct posture image, and alerting the user in response to the difference between the estimated azimuth and elevation image and the nearest correct posture image exceeding a preset threshold. In some embodiments, generating the second data comprises generating macro-doppler data according to second reflected signal and generating estimated doppler data according to the macro-doppler data, where generating the first data comprises generating vital-doppler data according to the estimated doppler data and the first reflected signal. In some embodiments, the method further includes receiving a third reflected signal that is a third reflection of a radar beam from legs of the user on the belt, determining, according to the second reflected signal, leg doppler data, determining a travelled distance for the user according to the first reflected signal, determining a calorie burned amount according to the traveled distance for the user, and displaying the travelled distance and the calorie burned amount on the display.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A treadmill, comprising:
   a belt;
   a display;
   a first sensor having first transmission circuitry for transmitting a first radar beam over the belt and first reception circuitry for detecting a first reflected signal that is a reflection of the first radar beam from a user on the belt, wherein the first transmission circuitry is configured to transmit a first portion of the first radar beam in a frequency modulated continuous wave (FMCW) mode during a first observation window, and transmit a second portion of the first radar beam in an interferometric mode during a second observation window different from the first observation window;
   a processor connected to the first sensor, the belt and the display; and
   a non-transitory computer-readable storage medium storing a program to be executed by the processor, the program including instructions for:
      generating second data from the first portion of the first radar beam;
      generating vital-doppler data from the second portion of the first radar beam;
      determining, according to the first reflected signal, first data associated with a vital sign of the user according to the vital-doppler data; and
      displaying, according to the first data, the vital sign on the display.

2. The treadmill of claim 1, wherein the program further includes instructions for:
   detecting, according to the first reflected signal, a gesture of the user while the user is on the belt; and
   controlling at least one of the belt and the display according to the gesture.

3. The treadmill of claim 2, wherein
   second data is estimated range and macro-doppler data.

4. The treadmill of claim 3, wherein the program further includes instructions for:
   determining a user positon according to the estimated range and macro-doppler data; and
   adjusting an operating parameter of the belt according to the user position.

5. The treadmill of claim 4, wherein the instructions for determining the user positon include instructions for determining a measured user position according to the estimated range and macro-doppler data; and
   wherein the instructions for adjusting the operating parameter of the belt include instructions for adjusting at least one of a speed or an incline of the belt according to a predicted user position determined using a Kalman filter and according to the measured user position.

6. The treadmill of claim 3, wherein the program further includes instructions for determining a user gesture according to the macro-doppler data; and
   controlling the display according to the user gesture.

7. The treadmill of claim 3, wherein the instructions for generating the macro-doppler data from the first portion of the first radar beam include instructions for generating estimated doppler data according to the macro-doppler data; and
   wherein the instructions for determining first data associated with the vital sign of the user includes instructions for determining the first data associated with the vital sign of the user according to the vital-doppler data and the estimated doppler data.

8. The treadmill of claim 1, further comprising a second sensor having second transmission circuitry for transmitting a second radar beam over the belt and second receiving circuitry for detecting a second reflected signal that is a reflection of the second radar beam from legs of the user on the belt;
   wherein the program further includes instructions for:
      determining, according to the second reflected signal, leg doppler data;
      determining a travelled distance for the user according to the first reflected signal;
      determining a calorie burned amount according to the traveled distance for the user; and
      displaying the travelled distance and the calorie burned amount on the display.

9. A method, comprising:
   receiving, by a first sensor of a treadmill, a first reflected signal that is a first reflection of a first radar beam reflected from a user on a belt of the treadmill, wherein the first radar beam is a first portion of a radar transmission in a frequency modulated continuous wave (FMCW) mode during a first observation window;
   receiving, by a second sensor of a treadmill, a second reflected signal that is a second reflection of a second radar beam reflected from the user, wherein the second radar beam is a second portion of the radar transmission in an interferometric mode during a second observation window;
   generating, as macro-doppler data according to the first reflected signal, first data associated at least one of a gesture of the user or a position of the user on the belt;
   generating, as vital-doppler data according to the second reflected signal, second data associated with a vital sign of the user;
   controlling at least one of the belt and a display of the treadmill according to the first data; and
   displaying, according to the second data, the vital sign on the display.

10. The method of claim 9, wherein the second observation window is different from the first observation window; and.

11. The method of claim 10, further comprising:
    determining a measured user position according to the macro-doppler data;

determining a predicted user position using a Kalman filter and according to the measured user position; and adjusting at least one of a speed or an incline of the belt according to a predicted user position determined using a Kalman filter applied to the measured user position.

12. The method of claim 10, wherein the generating the macro-doppler data comprises generating estimated doppler data according to the macro-doppler data; and wherein the generating the second data associated with the vital sign of the user comprises generating the second data associated with the vital sign of the user according to the vital-doppler data and the estimated doppler data.

13. The method of claim 9, further comprising:

receiving a third reflected signal that is a third reflection of a radar beam from legs of the user on the belt;

determining, according to the third reflected signal, leg doppler data;

determining a travelled distance for the user according to the first reflected signal;

determining a calorie burned amount according to the traveled distance for the user; and displaying the travelled distance and the calorie burned amount on the display.

14. A method, comprising:

moving a belt of a treadmill;

transmitting a first radar beam, using an interferometric mode in an interferometric observation window of a radar transmission, over the belt toward a user on the belt while the belt is moving;

transmitting a second radar beam over the belt toward the user while the belt is moving and using a frequency modulated continuous wave (FMCW) mode in an FMCW observation window of the radar transmission;

detecting a first reflected signal that is a first reflection of the first radar beam from the user;

detecting a second reflected signal that is a second reflection of the second radar beam from the user;

generating, according to the first reflected signal, first data associated with a vital sign of the user;

generating, according to the second reflected signal, second data associated with a gesture of the user;

controlling the display according to the second data; and displaying, according to the first data, the vital sign on a display of the treadmill.

15. The method of claim 14, further comprising:

detecting, according to the second data, the gesture;

wherein the controlling the display according to the second data comprises controlling the display according to the gesture.

16. The method of claim 15, wherein the interferometric observation window is different from the FMCW observation window.

17. The method of claim 15, further comprising:

determining a measured user position according to the second reflected signal;

determining a predicted user position using a Kalman filter and according to the measured user position; and adjusting at least one of a speed or an incline of the belt according to a predicted user position determined using a Kalman filter and according to the measured user position.

18. The method of claim 15, further comprising:

determining a an estimated azimuth and elevation image according to the second reflected signal and indicative of a posture of the user;

determining a nearest correct posture image for the estimated azimuth and elevation image from a set of saved two dimensional (2D) elevation and azimuth images of correct postures;

determining a difference between the estimated azimuth and elevation image and the nearest correct posture image; and alerting the user in response to the difference between the estimated azimuth and elevation image and the nearest correct posture image exceeding a preset threshold.

19. The method of claim 15, wherein the generating the second data comprises generating macro-doppler data according to second reflected signal and generating estimated doppler data according to the macro-doppler data;

wherein the generating the first data comprises generating vital-doppler data according to the estimated doppler data and the first reflected signal.

20. The method of claim 15, further comprising:

receiving a third reflected signal that is a third reflection of a radar beam from legs of the user on the belt;

determining, according to the second reflected signal, leg doppler data;

determining a travelled distance for the user according to the first reflected signal;

determining a calorie burned amount according to the traveled distance for the user; and displaying the travelled distance and the calorie burned amount on the display.

* * * * *